United States Patent
Chouinard et al.

(12)

(10) Patent No.: US 6,942,693 B2
(45) Date of Patent: Sep. 13, 2005

(54) BRAIDED BRANCHING STENT, METHOD FOR TREATING A LUMEN THEREWITH, AND PROCESS FOR MANUFACTURE THEREOF

(75) Inventors: Paul F. Chouinard, Maple Grove, MN (US); Dennis A. Peiffer, Maple Grove, MN (US); Patrick A. Haverkost, Brooklyn Center, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 491 days.

(21) Appl. No.: 10/115,221

(22) Filed: Apr. 3, 2002

(65) Prior Publication Data

US 2002/0111674 A1 Aug. 15, 2002

Related U.S. Application Data

(62) Division of application No. 09/494,704, filed on Jan. 31, 2000, now Pat. No. 6,398,807.

(51) Int. Cl.[7] .................................................. A61F 2/06
(52) U.S. Cl. ...................................... 623/1.35; 623/1.53
(58) Field of Search ............................... 623/1.53, 1.15, 623/1.22, 1.35; 87/8, 11, 33, 41

(56) References Cited

U.S. PATENT DOCUMENTS

| 2,388,693 A | 11/1945 | Jeckel |
| 4,620,473 A | 11/1986 | Bull |
| 4,621,560 A | 11/1986 | Brown et al. |

(Continued)

FOREIGN PATENT DOCUMENTS

| EP | 0 800 801 | 10/1997 |
| EP | 0 804 909 | 11/1997 |
| FR | 2 678 508 | 8/1993 |
| FR | 2765097 | 6/1997 |
| WO | WO 98/19630 | 5/1998 |
| WO | WO 98/22159 | 5/1998 |
| WO | WO 99/25271 | 5/1999 |
| WO | WO 99/55256 | 11/1999 |
| WO | WO 00/09059 | 2/2000 |
| WO | WO 00/44309 | 8/2000 |
| WO | WO 01/54621 | 8/2001 |

OTHER PUBLICATIONS

U.S. Appl. No. 09/442,165, Chouinard et al., filed Nov. 17, 1999.
U.S. Appl. No. 09/442,192, Zarbatany et al., filed Nov. 16, 1999.
International Search Report dated May 30, 2001.

*Primary Examiner*—Julian W. Woo
(74) *Attorney, Agent, or Firm*—RatnerPrestia

(57) ABSTRACT

A bifurcated, braided stent has a body that branches into a plurality of legs and is adapted for deployment in a lumen. At least a portion of each leg of the stent comprises a discrete plurality of continuous filaments braided together, and at least a portion of the body comprises one or more of the continuous filaments from each of the legs braided together. The stent can be used for treating a diseased bifurcated lumen of a human being by deploying the stent therein. The stent can be constructed by a process comprising braiding each plurality of filaments to form the leg sections, and braiding one or more filaments from each plurality of filaments together to form the body. The process may be performed by creating the legs first and then the body, or vice versa. The stent may be constructed on a mandrel using a braiding machine.

22 Claims, 13 Drawing Sheets

U.S. PATENT DOCUMENTS

| | | |
|---|---|---|
| 4,655,771 A | 4/1987 | Wallsten |
| 4,881,444 A | 11/1989 | Krauland |
| 4,885,973 A | 12/1989 | Spain |
| 4,994,071 A | 2/1991 | MacGregor |
| 5,064,435 A | 11/1991 | Porter |
| 5,398,586 A | 3/1995 | Akiyama et al. |
| 5,485,774 A | 1/1996 | Osborne |
| 5,578,072 A | 11/1996 | Barone et al. |
| 5,609,627 A | 3/1997 | Goicoechea et al. |
| 5,632,772 A * | 5/1997 | Alcime et al. ............. 623/1.35 |
| 5,669,924 A * | 9/1997 | Shaknovich ............... 623/1.35 |
| 5,718,159 A | 2/1998 | Thompson |
| 5,741,235 A | 4/1998 | Knight |
| 5,741,333 A | 4/1998 | Frid |
| 5,755,778 A | 5/1998 | Kleshinski |
| 5,758,562 A | 6/1998 | Thompson |
| 5,906,641 A | 5/1999 | Thompson et al. |
| 5,957,974 A | 9/1999 | Thompson et al. |
| 5,972,017 A | 10/1999 | Berg et al. |
| 6,019,786 A | 2/2000 | Thompson |
| 6,080,191 A | 6/2000 | Summers |
| 6,083,257 A | 7/2000 | Taylor et al. |
| 6,117,167 A | 9/2000 | Goicoechea et al. |
| 6,136,022 A | 10/2000 | Nunez et al. |
| 6,156,064 A | 12/2000 | Chouinard |
| 6,159,239 A | 12/2000 | Greenhalgh |
| 6,409,750 B1 | 6/2002 | Hyodoh et al. |

\* cited by examiner

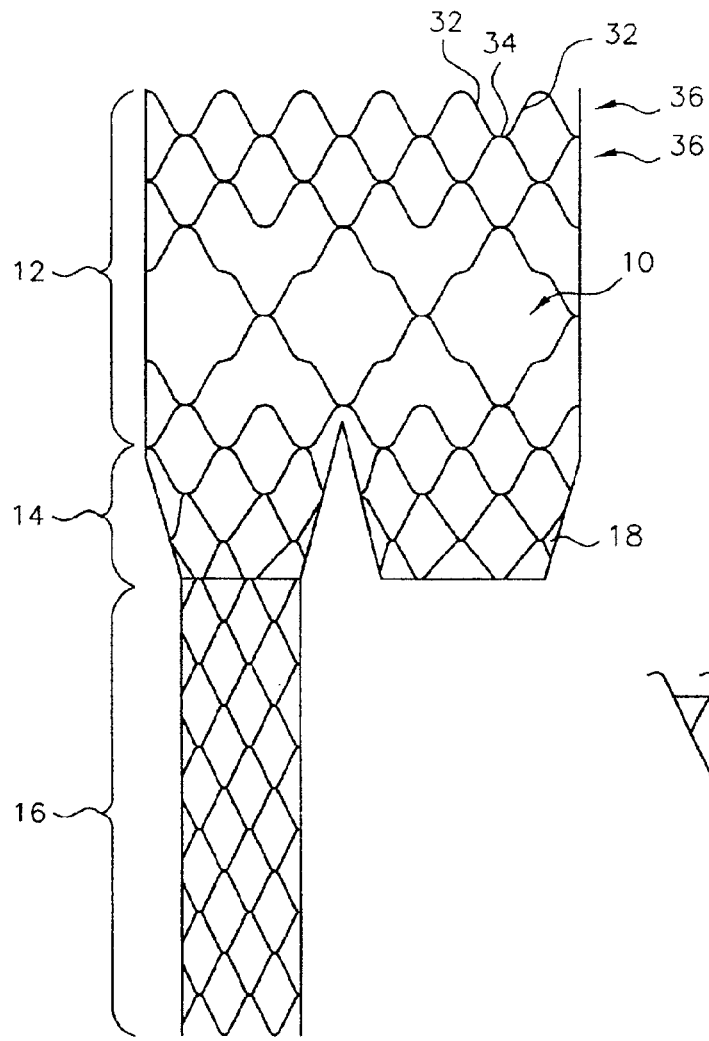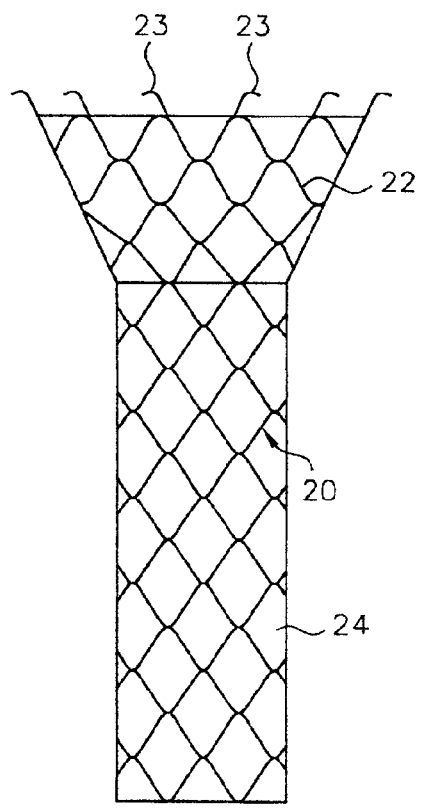
FIG. 1A
(Prior Art)
FIG. 1B
(Prior Art)

BRAIDED BRANCHING STENT, METHOD FOR TREATING A LUMEN THEREWITH, AND PROCESS FOR MANUFACTURE THEREOF

RELATED APPLICATIONS

This application is a divisional of U.S. patent application Ser. No. 09/494,704, filed Jan. 31, 2000 now U.S. Pat. No. 6,398,807, which is related to U.S. patent application Ser. No. 09/494,980, filed Jan. 31, 2000 (U.S. Pat. No. 6,325, 822), titled "BRAIDED STENT HAVING TAPERED FILAMENTS" by Chouinard, Haverkost, Peiffer, and Roberts.

TECHNICAL FIELD

This invention relates generally to endoluminal stents, grafts, and/or prostheses and, more specifically, to braided stents adapted for deployment in branched lumina and processes for their manufacture.

BACKGROUND OF THE INVENTION

A stent is an elongated device used to support an intraluminal wall. In the case of a stenosis, a stent provides an unobstructed conduit for blood in the area of the stenosis. Such a stent may also have a prosthetic graft layer of fabric or covering lining the inside or outside thereof, such a covered stent being commonly referred to in the art as an intraluminal prosthesis, an endoluminal or endovascular graft (EVG), or a stent-graft.

A prosthesis may be used, for example, to treat a vascular aneurysm by removing the pressure on a weakened part of an artery so as to reduce the risk of rupture. Typically, a prosthesis is implanted in a blood vessel at the site of a stenosis or aneurysm endoluminally, i.e. by so-called "minimally invasive techniques" in which the prosthesis, restrained in a radially compressed configuration by a sheath or catheter, is delivered by a deployment system or "introducer" to the site where it is required. The introducer may enter the body through the patient's skin, or by a "cut down" technique in which the entry blood vessel is exposed by minor surgical means. When the introducer has been threaded into the body lumen to the prosthesis deployment location, the introducer is manipulated to cause the prosthesis to be ejected from the surrounding sheath or catheter in which it is restrained (or alternatively the surrounding sheath or catheter is retracted from the prosthesis), whereupon the prosthesis expands to a predetermined diameter at the deployment location, and the introducer is withdrawn. Stent expansion may be effected by spring elasticity, balloon expansion, or by the self-expansion of a thermally or stress-induced return of a memory material to a pre-conditioned expanded configuration.

Various types of stent architectures are known in the art, including many designs comprising a filament or number of filaments, such as a wire or wires, wound or braided into a particular configuration. Included among these wire stent configurations are braided stents, such as is described in U.S. Pat. No. 4,655,771 to Hans I. Wallsten and incorporated herein by reference, the '771 Wallsten patent being only one example of many variations of braided stents known in the art and thus not intended as a limitation of the invention described herein later. Braided stents tend to be very flexible, having the ability to be placed in tortuous anatomy and still maintain patency. The flexibility of braided stents make them particularly well-suited for treating aneurysms in the aorta, where the lumen of the vessel often becomes contorted and irregular both before and after placement of the stent.

Among the many applications for stent-grafts is for deployment in bifurcated lumen, such as for repair of abdominal aortic aneurysms (AAA). Various stent-graft configurations are known in the art for bifurcated applications, including single-piece and modular designs, graft designs fully supported by stents, and graft designs only partially supported by stents. Referring now to FIGS. 1A and 1B, there are shown the components of a modular, non-braided, bifurcated, stent 10 for use with a fully-supported graft as is fully described in U.S. 5,609,627 to Goicoechea et al and adapted for implantation within the aorta of a human. By "fully-supported" it is meant that the graft is adapted to have stent structure underlying the graft throughout the entire length of the graft, as opposed to having extensive lengths of unsupported graft between anchoring stent portions, as will be described herein later.

As shown in FIG. 1A, stent 10 comprises a main body 12 which bifurcates into a first frustoconical leg transition 14 with a dependent first leg 16, and a second frustoconical leg transition 18. Second leg 20 is a modular component comprising a frustoconical part 22 adapted to interlock within second leg transition 18, and a depending portion 24. Frustoconical part 22 may have barbs 23 to help firmly connect second leg 20 to leg transition 18. As shown in FIG. 2, such a bifurcated stent 10 is typically implanted within the vasculature such that the main body 12 and leg transitions 14 and 18 are positioned within the aorta main portion 26 and with the dependent first leg 16 and depending portion 24 of second leg 20 each positioned within respective iliac arteries 28 and 30. Modular designs are also available wherein both legs are modular components. All of the bifurcated stents described herein, regardless of underlying structure, generally resemble the configuration shown in FIG. 2 when fully implanted.

As shown in FIGS. 1A and 1B and as fully described in the '627 patent, the structure of stent 10 is a continuous wire zig-zag structure comprising a series of struts 32 joined at apices 34 and wound into hoops 36, with abutting hoops joined together in some manner, such as with sutures, at abutting apices. One potential disadvantage of zig-zag stent architecture is that the apices of the zig-zag structure can rub against the graft, causing wear in the graft.

Modular, fully-supported, bifurcated stent-graft designs using braided architecture are also known. Such designs typically comprise a tubular stent that is crimped or pinched together in the middle or at one end to form a septum and two smaller lumina. These two lumina can then be used as sockets for the iliac sections. The braided stents have the advantage of being very adaptable to tortuous anatomy as compared to other stent architectures. The formation of the crimp, however, can cause metal cold-work and embrittlement in the stent wires and can result in bulkiness in the bifurcation region, requiring a relatively larger deployment profile than other designs.

To overcome the potential disadvantages of modular designs, it is also known to provide one-piece or "unitary" stent designs. Such known designs may be fully supported or only partially supported, such as by having anchoring stent portions only located at the end sections adjacent each opening of the graft. One piece stent designs having a zig-zag stent architecture still have the same disadvantage of potential graft wear due to rubbing of the apices. One-piece graft designs that are only partially supported have the potential disadvantage that the differences in radial strength and flexibility between the unsupported and supported regions makes the stent-grafts susceptible to kinking when navigating through tortuous lumina.

Thus, there is still a need in the art to provide a fully-stent-supported, bifurcated stent-graft that is flexible for navigation through tortuous lumina and that minimizes the risk of elements of the stent architecture creating wear in the graft covering or liner.

SUMMARY OF THE INVENTION

The invention comprises a branching stent for deployment in a lumen, the stent comprising a body that branches into a plurality of legs. At least a first leg portion of each leg comprises a discrete plurality of continuous filaments braided together and at least a first body portion of the body comprises at least one (preferably more, and more preferably all) of the continuous filaments from each discrete plurality of continuous filaments braided together. At least one of the legs or the body may further comprise a second portion thereof having a non-braided stent architecture, or each of the legs and the body may further comprise a braided stent architecture throughout the entire respective lengths thereof. The stent may be a bifurcated stent having an interface between the body and the legs with an open crotch region between the legs at the interface or a closed crotch region between the legs at the interface. A stent with a closed crotch may further comprise an open hip region.

The invention also comprises a stent for deployment in a lumen, the stent comprising a plurality of continuous filaments braided together, at least one filament comprising a tapered filament having at least one first region having a first, relatively-larger cross-sectional area and at least one second region having a second, relatively-smaller cross-sectional area. A braided stent having tapered wire according to the present invention may be a bifurcated stent or a non-bifurcated stent.

The invention also comprises a method for treating a diseased branched lumen of a human being, the branched lumen comprising a main section that branches into a plurality of branches. The method comprises the step of deploying within the branched lumen a branching stent comprising a body that branches into a plurality of legs. At least a first leg portion of each leg comprises a discrete plurality of continuous filaments braided together, and at least a first body portion of the body comprises at least one of the continuous filaments from each discrete plurality of continuous filaments braided together. The deployment step comprises deploying the body in the main section and deploying each leg within one of the branches.

The invention further comprises a process for constructing a braided, branched stent having a body and a plurality of legs, each leg comprising a discrete plurality of filaments, the process comprising the steps of: (a) braiding each plurality of filaments to individually form at least first leg portions of each of the legs; and (b) braiding at least one filament from each plurality of continuous filaments together to form a first body portion of the body. Step (a) may comprise the steps of: (i) braiding a first discrete plurality of filaments to form the first leg; and (ii) braiding a second discrete plurality of filaments to form the second leg, and step (b) may comprise braiding the first plurality of filaments and the second plurality of filaments together to form the body. Step (a) may be performed prior to step (b), or vice versa. The stent may be braided around a mandrel having a mandrel body, a first detachable mandrel leg, and a second detachable mandrel leg. In such case, step (a)(i) comprises braiding the first plurality of filaments about the first detachable mandrel leg, step (a)(ii) comprises braiding the second plurality of filaments about the second detachable mandrel leg, and step (b) comprises braiding the first plurality of filaments and second plurality of filaments together about the mandrel body.

The braiding may be performed on a braiding machine having a predetermined plurality of bobbin carriers adapted to revolve in a pattern about a longitudinal axis. A first set of bobbin carriers may be adapted to revolve in a first circumferential direction and a second set of bobbin carriers may be adapted to revolve in a second circumferential direction, each bobbin carrier adapted to carry at least one bobbin. Each bobbin is adapted to provide one or more filaments for braiding within the stent. In such case, step (a)(i) comprises using filaments from a first portion of the predetermined plurality of bobbins to braid the first leg about the first detachable mandrel leg positioned substantially along the longitudinal axis in a braiding zone. The braiding zone is defined as a conical zone defined by the filaments extending from the bobbins to the stent on the mandrel. In step (a)(ii), the process comprises using filaments from a second portion of the predetermined plurality of bobbins to braid the second leg about the second detachable mandrel leg positioned in the braiding zone. Step (b) comprises using filaments from both portions of the predetermined plurality of bobbins to braid the body about the mandrel body positioned in the braiding zone.

Thus, the process may further comprise the steps of: (A) first performing step (a)(i); (B) then removing the first portion of the predetermined plurality of bobbins from the braiding machine and removing the first mandrel leg from the braiding zone; (C) then performing step (a)(ii); (D) then returning the first portion of the predetermined plurality of bobbins to the braiding machine, attaching the first mandrel leg and the second mandrel leg to the mandrel body, and positioning the mandrel body in the braiding zone; and (E) then performing step (b). The process may instead comprise the reverse: (A) first performing step (b); (B) then removing the second portion of the predetermined plurality of bobbins from the braiding machine and attaching the first mandrel leg to the mandrel body; (C) then performing step (a)(i); (D) then returning the second portion of the predetermined plurality of bobbins to the braiding machine and removing the first portion of the predetermined plurality of bobbins from the braiding machine, attaching the second mandrel leg to the mandrel body, detaching the first mandrel leg from the mandrel body, and positioning the first leg of the stent outside the braiding zone so that the first leg does not interfere with performance of step (a)(ii); and (E) then performing step (a)(ii).

BRIEF DESCRIPTION OF DRAWINGS

The invention is best understood from the following detailed description when read in connection with the accompanying drawing. It is emphasized that, according to common practice, some of the features of the drawing are not to scale. On the contrary, the dimensions of some of the features are arbitrarily expanded or reduced for clarity. Included in the drawing are the following figures:

FIG. 1A is a front view of one stent component of an exemplary bifurcated intraluminal stent known in the art.

FIG. 1B is a front view of a mating stent component adapted to be connected to the bifurcated stent component of FIG. 1A.

DETAILED DESCRIPTION OF INVENTION

The entire disclosure of U.S. patent application Ser. No. 09/494,704, filed Jan. 31, 2000, is expressly incorporated by reference herein.

The invention will next be illustrated with reference to the figures wherein similar numbers indicate the same elements in all figures. Such figures are intended to be illustrative rather than limiting and are included herewith to facilitate the explanation of the apparatus of the present invention.

Figure 2:
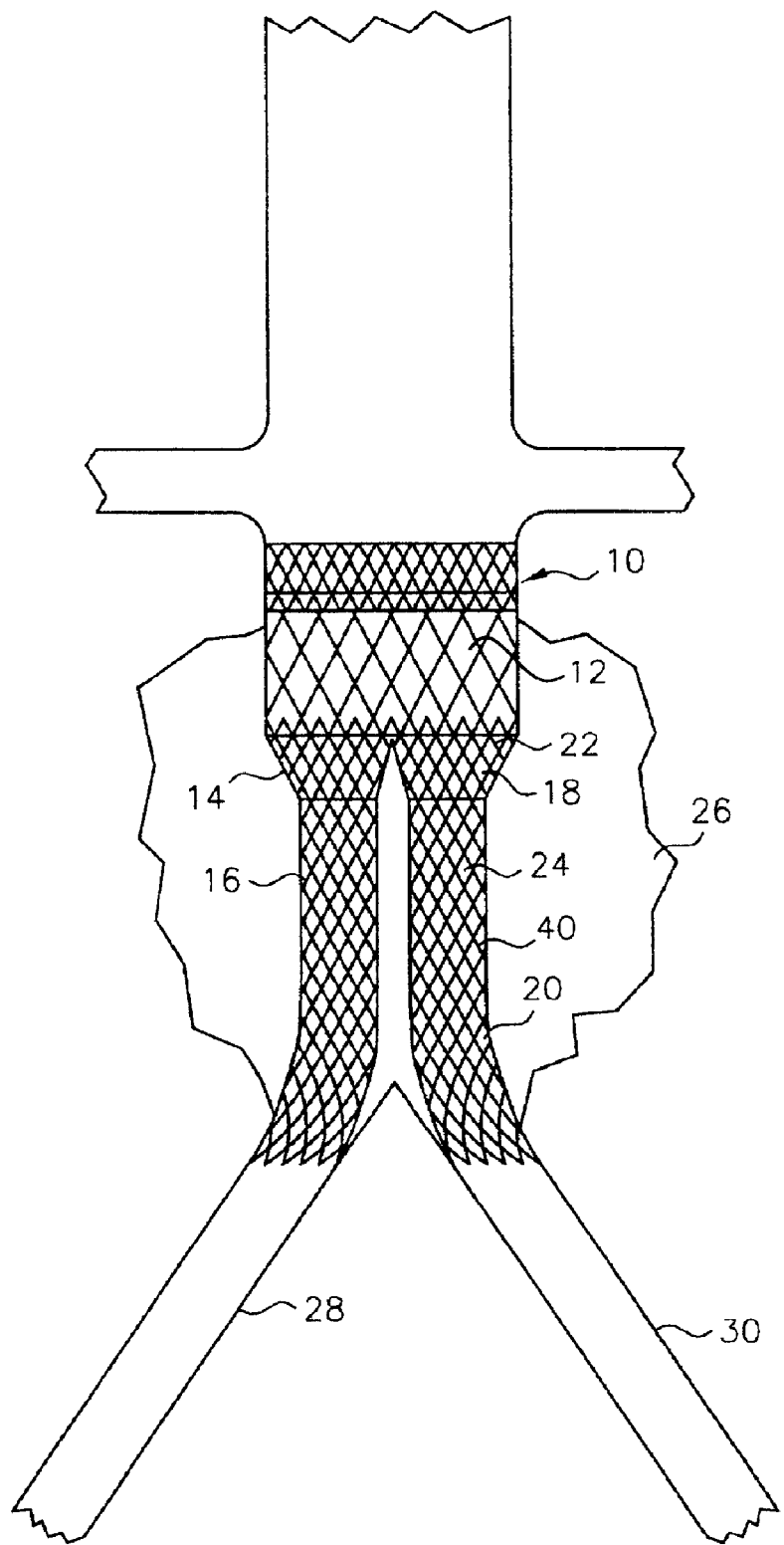
FIG. 2 is a front view of the stent components shown in FIG. 1A and FIG. 1B in an assembled configuration implanted in the aortic region of a human, as is known in the art.
Figure 3:
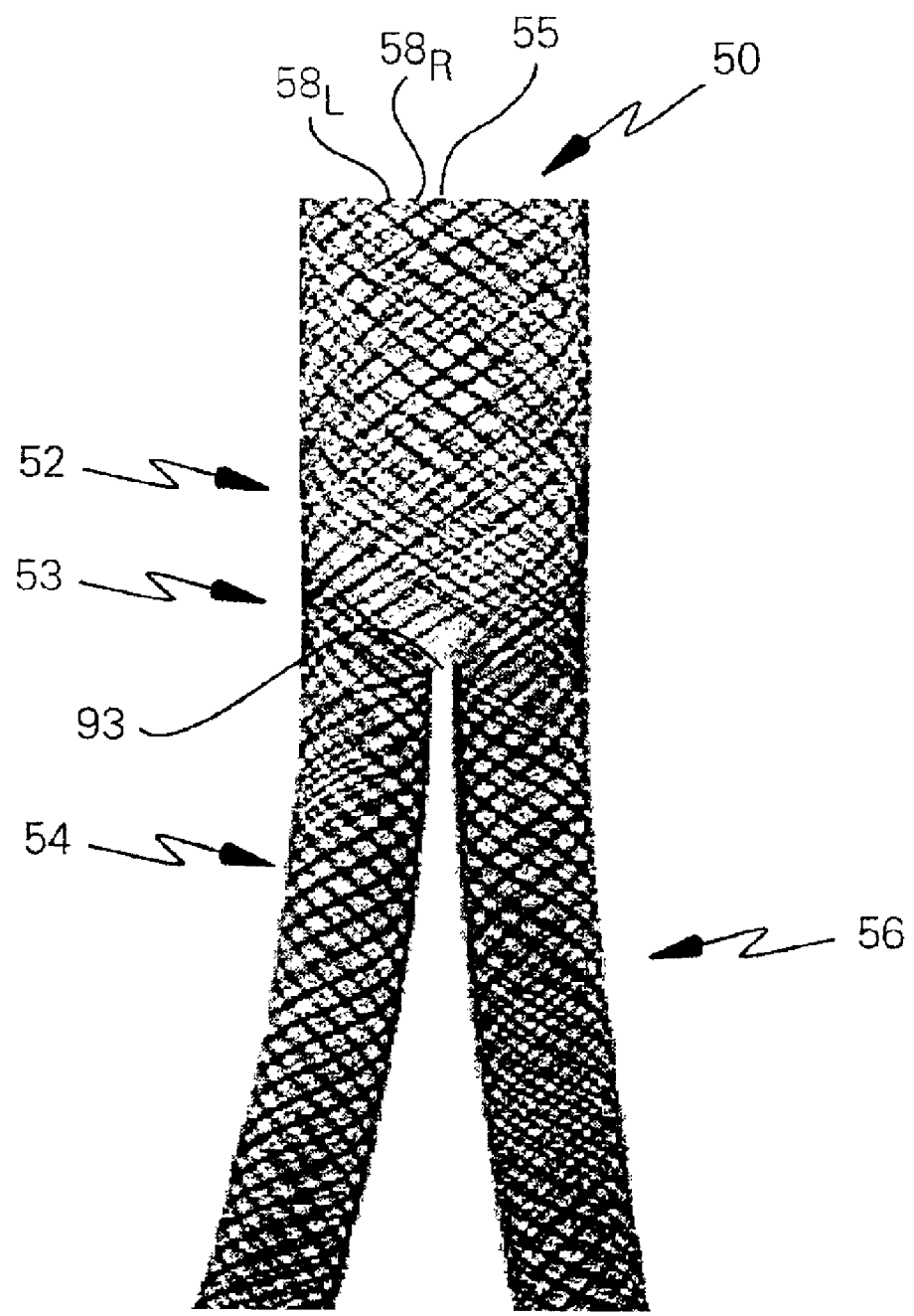
FIG. 3 is a front view of a portion of an exemplary stent embodiment having an open crotch according to the present invention.

Referring now to FIG. 3, there is shown a bifurcated, braided stent 50 according to the present invention. As shown in FIG. 3, the stent comprises a trunk section 52, a first iliac leg 54 and a second iliac leg 56. Stent 50 as shown in FIG. 3 is a unitary stent. That is, iliac legs 54 and 56 are continuous with trunk section 52, unlike modular stent designs in which two or more stent segments are assembled together to form the various parts of the stent (e.g., the trunk section and the two legs). As used herein, the term "unitary" means a stent having portions of each of its various parts made as a single unit. Thus, a unitary stent contemplates a stent whose entire length of all of its parts are made as a single unit, without the need to attach additional stent segments upon deployment. In addition, a unitary stent may be used in conjunction with stent segments, if it is desired to attach such segments to either the legs or the trunk section upon deployment.

It should be noted herein that unitary stent 50 as shown in FIG. 3 is merely one exemplary embodiment, and that this invention is applicable to "modular", braided stents as well. As used herein, the term "modular" means a stent having at least two discrete portions adapted for assembly in situ. As is well-known in the art, one type of exemplary modular bifurcated stent may include a trunk section that bifurcates into a single leg on one side adapted to extend into one iliac, and a socket on the other side, with the other leg being a modular piece adapted to be inserted into the socket, similar to the configuration shown in FIGS. 1A and 1B. Another type of modular bifurcated stent may comprise only a trunk section with a bifurcated region that terminates is two short sockets into which two discrete leg members are adapted to be inserted. Although not depicted herein, such general configurations are well-known in the art, and when fully assembled, resemble the unitary configurations depicted in FIGS. 3 and 8, except that there is an overlap region where each leg member is inserted into each socket as is well-known in the art. The term "leg" as used herein with respect to a stent having a body portion and leg portions may refer to a full, integral leg adapted to, for example, extending into an iliac artery, or may refer to a socket portion of a leg adapted to receive a modular leg element. Thus, although the invention as illustrated and described herein primarily references full leg structures, each of the methods and structures described herein is equally applicable to partial leg structures such as sockets for receiving modular leg elements.

Bifurcated region 53 as shown in FIG. 3, rather than being a crimped or pinched region, is formed by the weave of the stent filaments 58R and 58L. As can be seen in FIG. 3, a typical braided stent comprises a first set of filaments 58L wound in a first helical direction (to the left as shown in FIG. 3) and a second set of filaments 58R wound in a second, opposite helical direction (to the right as shown in FIG. 3), forming a plurality of overlaps 55. Filaments 58L and 58R may be wire, such as nitinol or stainless steel, or may comprise polymer or any type of filaments known in the art.

As used herein, a "braided" stent refers to a stent formed of at least two continuous filaments which are interwoven in a pattern, thus forming overlaps 55, as shown in FIG. 3. At each overlap, one filament is positioned radially outward relative to the other filament. Following each filament along its helical path through, a series of consecutive overlaps, that filament may, for example be in the radial inward position in one overlap and in the radial outward position in a next overlap, or may in the inward position for two overlaps and in the outward position for the next two, and so on. As mentioned above, exemplary braided stents are disclosed in U.S. Pat. No. 4,655,771 to Hans I. Wallsten. A typical braided stent is formed on a mandrel by a braiding or plaiting machine, such as a standard braiding machine known in the art and manufactured by Rotek of Ormond Beach, Fla. Any such braiding or plaiting machine may be used, however, and the use of terminology specific to components of the machine manufactured by Rotek is not intended as a limitation to the use of that machine design. To the extent that the terminology used herein is specific to the components of any one or several machines, it should be understood such components specifically referred to herein generally have corresponding functionally equivalent components with respect to other machines. Thus, the scope of the method described and claimed herein for braiding the stent of present invention is not intended to be limited to the specific machine embodiment described herein, but extends to functionally equivalent machines also.

Figure 4A:
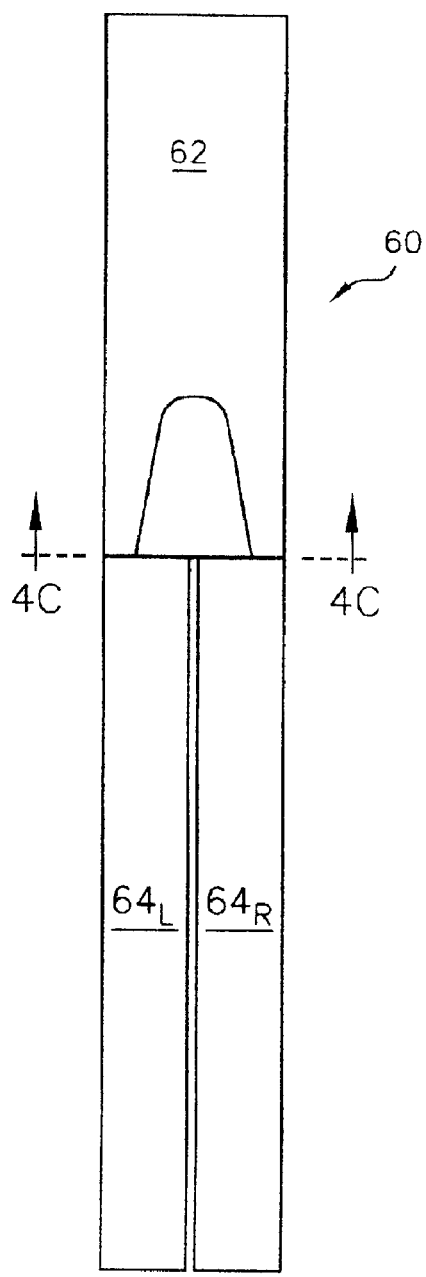
FIG. 4A is a front view of an exemplary assembled modular mandrel in accordance with this invention.
Figure 4B:
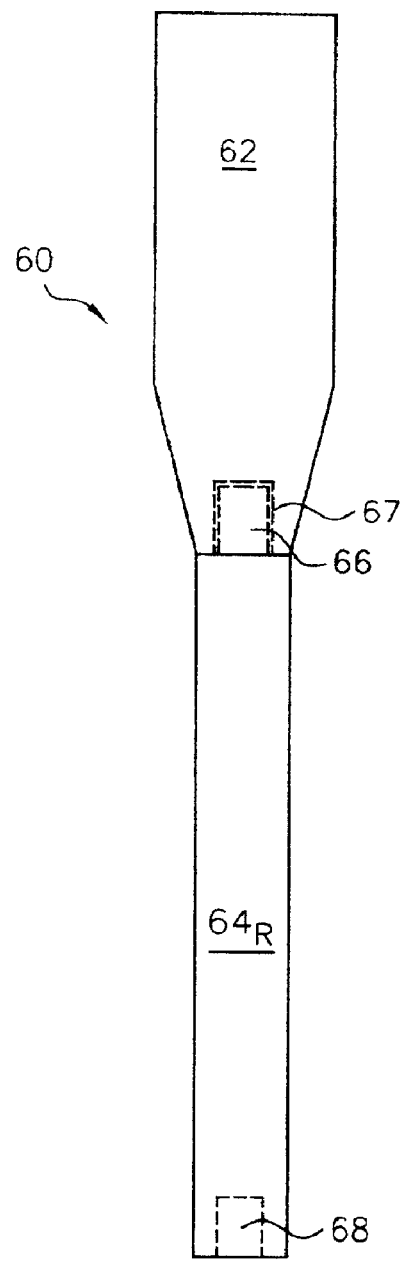
FIG. 4B is a right side view of the assembled modular mandrel of FIG. 4A, showing hidden components (not shown in FIG. 4A) with dashed lines.
Figure 4C:
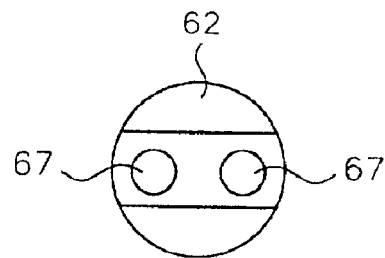
FIG. 4C is a bottom view of the trunk mandrel portion of the mandrel of FIG. 4A.

Braiding machines can be used for manufacturing the stent of the present invention about an exemplary modular mandrel as shown in FIGS. 4A–C. Modular mandrel 60 as shown from the front in FIG. 4A and from the side in FIG. 4B, comprises a large diameter trunk section 62 and two, smaller diameter leg sections $64_L$ and $64_R$. Leg sections 64 may comprise a male connector 66, as shown in FIG. 4B, which mates with a female receptacle 67 in trunk section 62 as shown in FIGS. 4B and 4C. Hidden lines are not shown in FIG. 4A. Conversely, the female receptacle may be on leg sections $64_L$ and $64_R$ and the male connector on trunk section 62. Connector 66 and receptacle 68 may be threaded, may comprise slip fittings, or may otherwise enable leg sections $64_L$ and $64_R$ to be releasably connected trunk section 62. Tapered recess 69 serves to model the stent gradually to the different diameters of an aorta and iliac arteries.

Referring now to FIGS. 5A–F, braiding machine 70 is shown schematically as typically comprising a number of notch gears 72 arranged in a circle. Machine 70 shown in FIGS. 5A–F has twenty such notch gears 72, each notch gear adapted to rotate in the opposite direction as its neighboring notch gears, as illustrated by arrows A and B. This counter-rotation passes bobbin carriers 71, and the bobbins 74 mounted thereon, in a sinusoidal fashion from gear to gear, thus causing the bobbins to revolve about a longitudinal axis on which the circle is centered. The configuration of the notch gears, bobbin carriers, and bobbins to achieve this movement are well-known in the art, and an example of such a configuration is found in the braiding machine manufactured by Rotek.

Figure 5A:
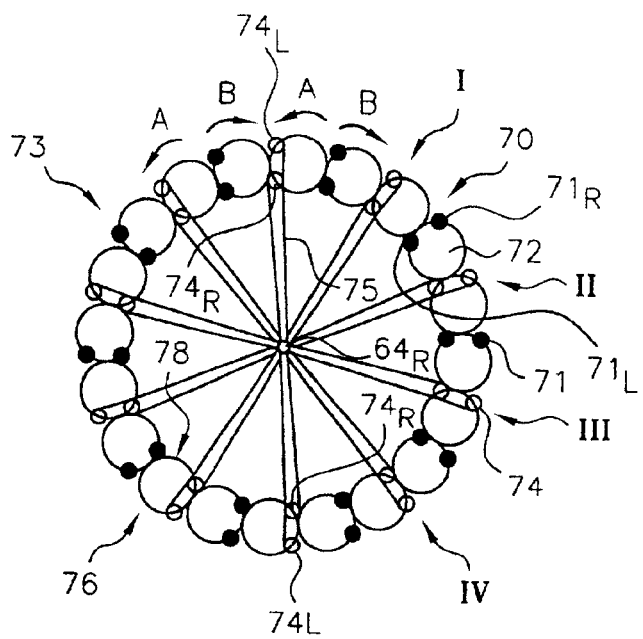
FIG. 5A is a front view of the notch gears of a braiding machine, loaded with the first set of wire bobbins to form the first leg section of the braided stent about the first leg mandrel.

Each bobbin comprises wire 75 wound thereon. The bobbin carrier and bobbin typically interface in a way that helps keep the wire unraveling from the bobbin under proper tension, as is known in the art. Although the motion of the bobbins is described herein, it should be understood that the bobbins 74 are moved by virtue of being mounted on bobbin carriers 71. Thus, although empty bobbin carriers 71 are shown in FIG. 5A, for example, each bobbin 74 also is mounted upon a bobbin carrier, creating a "loaded" bobbin carrier. To reduce clutter in FIGS. 5A–5F, the underlying bobbin carrier is not shown for carriers loaded with bobbins 74. Bobbins 74L, shown in FIG. 5A with wire 75 unraveling from the left-hand side of the bobbin as viewed facing the bobbin from outside of the circle of notch gears 72, travel sinusoidally around the circle of notch gears 72 in a counterclockwise direction as viewed in FIG. 5A. Conversely, bobbins 74R with wire 75 unraveling from the right-hand side of the bobbin as viewed facing the bobbin from outside of the circle of notch gears 72, travel in a clockwise direction. Similarly, bobbin carriers 71L travel counterclockwise and carriers 71R travel clockwise.

Figure 6:
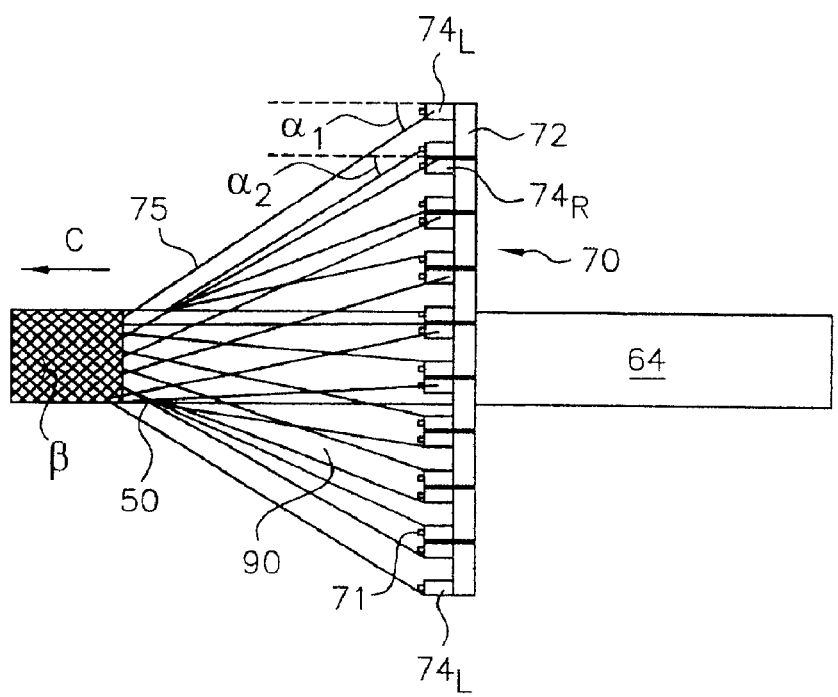
FIG. 6 is a side view of the notch gears in the braiding machine of FIG. 5A showing the conical configuration of the wires being braided about the mandrel.

The mandrel around which braided stent 50 is formed, such as leg mandrel 64R as shown in FIG. 5A, is moved in a controlled manner substantially along a longitudinal axis about which the circle of notch gears 72 is centered and about which the bobbin carriers 71 revolve. Thus, during processing, wires 75 extend from braiding machine 70 to mandrel 64 in a conical configuration, as shown in FIG. 6. As can be seen from FIG. 6, as two bobbins cross one another, their respective filaments form an overlap such that the filament from the bobbin on the outer radius 76 is disposed radially outward (with respect to the axis of the stent being assembled) relative to the filament from the bobbin on the inner radius 78. The space contained within the cone formed by the wires extending between the bobbins and the mandrel and including the space occupied by the mandrel is referred to herein as the "braiding zone" 90. Although the angles $\alpha_1$ and $\alpha_2$ of the wire to the mandrel may be varied as desired, $\alpha_1$ and $\alpha_2$ preferably each comprise an angle of approximately 55° when the braiding angle of a braided stent β is approximately 110°. This angle may vary dependent upon the exact radial position of the bobbin relative to the mandrel and whether the wire is on the inside radial position or outside radial position on an overlap. Note, for example, that when bobbin 74L is positioned radially outwardly with respect to bobbin 74R on gear 72, angle $\alpha_1$ is slightly larger than angle $\alpha_2$. As used herein, the phrase "substantially along the longitudinal axis" as used with respect to the alignment of the moving mandrel means that the mandrel does not have to be perfectly centered in the braiding zone, but merely needs to be aligned close enough to the longitudinal axis that the angles of the filaments between the mandrel and the bobbins allows the braiding operation to create a functional braid without tangling the filaments.

Mandrel leg sections $64_L$ and $64_R$ may therefore each comprise a puller interface 68 for attaching a "puller" adapted to pull the mandrel away from the circle of notch gears 72 at a controlled rate as the braid is formed. For example, puller interface 68 may be a drilled and tapped hole 68 in mandrel 64R as shown in FIG. 4B, and the puller may be a metal rod that has a threaded end or slip fitting adapted to be threaded or otherwise locked into the hole. The puller rod may be retracted away from the circle, for example, by a set of counter-rotating caterpillar tracks which hold the rod therebetween and move the rod in a controlled manner. Other types of pullers, methods of attachment of the puller to the mandrel, and means for moving the puller are also acceptable, and the invention is in no way limited to the exemplary configuration provided herein. In alternative machine designs, a "pusher" may be provided at the opposite end rather than a puller. Any means for axially moving the mandrel through braiding zone 90 is acceptable.

Figure 15C:
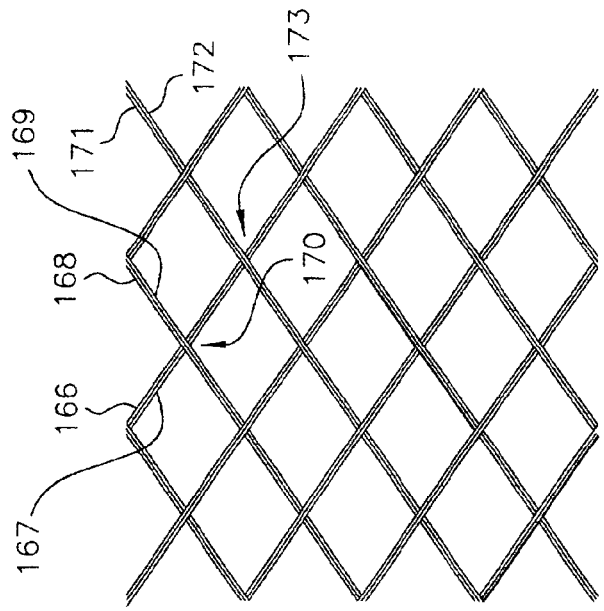
FIG. 15C depicts a portion of an exemplary stent embodiment having a 1:1 paired filament braiding ratio as is known in the art, the stent having been cut longitudinally and flattened.
Figure 15A:
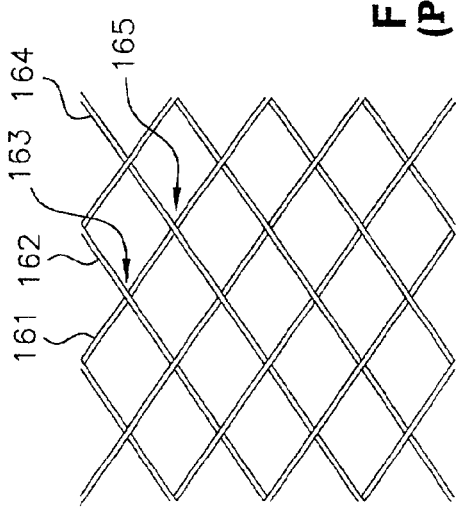
FIG. 15A depicts a portion of an exemplary stent embodiment having a 1:1 single filament braiding ratio as is known in the art, the stent having been cut longitudinally and flattened.

The circle of notch gears 72 can be considered to have an outer radius 76 (on which bobbins 74R are positioned in FIG. 5A) and an inner radius 78 (on which bobbins 74L are positioned in FIG. 5A). In the half-full configuration shown in FIG. 5A, each bobbin 74L crosses over one bobbin 74R while on outer radius 76 before returning to inner radius 78 and crossing under another bobbin 74R. The braid created by such a weave can be said to have a 1:1 single filament braiding ratio (because each single filament crosses under another single filament, then over one, then under one, and so on). The 1:1 single filament braiding ratio is illustrated in FIG. 15A. During the cross-over step where a bobbin on outer radius 76 crosses over a bobbin on inner radius 78, the difference between angle $\alpha_1$ and $\alpha_2$ is sufficient to assure that the wires clear one another without tangling.

To form a braid around a mandrel, wires 75 extending from bobbins 74 can be secured to the end of the mandrel in almost any manner, such as by taping them or tying them, and do not even have to be kept in any particular orientation. For example, all the wires may all be taped or tied to a single point on one side of the mandrel. Once the braiding machine starts, it will stabilize into the proper braid configuration after only a few circumferential hoops of overlaps 55 (shown in FIG. 3) are formed. The portion between the proper configuration and the end can either be cut away as scrap or unbraided and then manipulated to form a non-braided end winding, as is discussed herein later. In the alternative, to minimize scrap, the ends of wires 75 may be wound around pins (not shown) or otherwise secured to the mandrel in a spaced circumferential configuration similar to the configuration of bobbins 74 in braiding machine 70.

In one method for creating the braided bifurcated structure of the present invention, the braiding machine is first loaded as shown in FIG. 5A with a first portion 73 of a predetermined number of bobbins 74. The predetermined number of bobbins may comprise the maximum capacity of the machine and first portion 73 may, for example, comprise half of the bobbin capacity of the machine. The braiding operation is then performed as described above to form a first leg section of the braided stent around a first leg mandrel, for example leg mandrel 64R (either 64L or 64R may be the first leg mandrel, in which case the other is the second leg mandrel). After braiding the first leg section about mandrel first leg section 64R, bobbins 74 of first portion 73 can be regrouped to one side (the right side as shown in FIG. 5B) of the circle of notch gears 72.

Figure 14A:
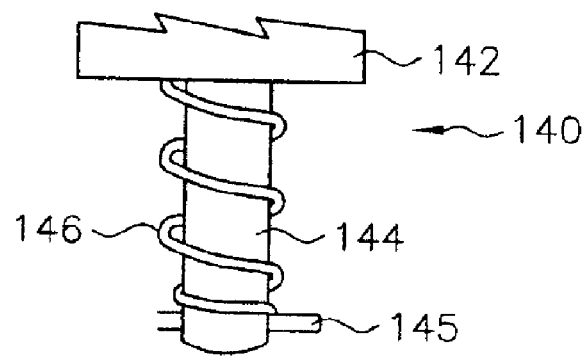
FIG. 14A depicts an exemplary side view of a male quick connect component that facilitates removal and replacement of the bobbin carrier in performing the method according to the present invention.
Figure 14B:
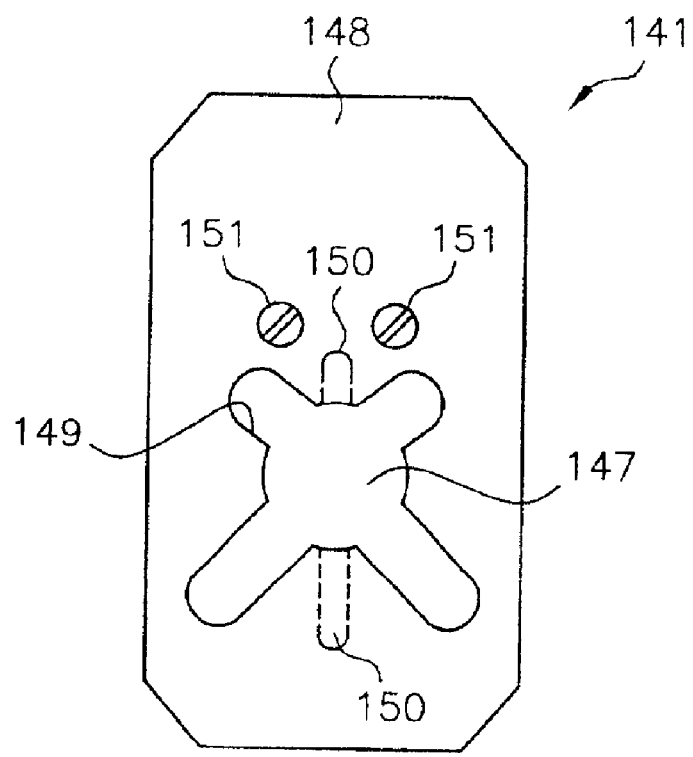
FIG. 14B depicts an exemplary plan view of a female quick connect component that facilitates removal and replacement of the bobbin carrier in performing the method according to the present invention.

The method for moving the bobbins may be by any of a number of ways. For example, certain bobbin carriers may comprise closed eyelets through which the wire is threaded, in which case the entire bobbin carrier may be removed. Other bobbin carriers, such as those manufactured, for example, by the Wardwell Braiding Machine Company of Central Falls, R.I., comprise open, curled guides resembling a "pigtail" such that the bobbins may be simply unlocked and lifted off of their respective bobbin carriers and the filament readily removed from the guide. It should be understood that as referred to herein, removing or replacing "the bobbins" on and off of the machine may comprise removing or replacing the bobbins only or the bobbins as still attached to the bobbin carriers. Where the entire bobbin carrier is removed, the bobbin carrier may be removed by simply removing any fasteners holding it in place, or to facilitate quicker removal and replacement, a quick-connect fitting can be used. The quick-connect fitting may comprise any number of means well-known in the art for providing an interlocking engagement of one element with another, such as a magnetic connection, a twist-and-lock connection, a spring-loaded ball in channel connection, a lever-controlled cam connection, or any connection known in the art. The configuration shown in FIGS. 14A and 14B is provided merely to show one example of such a quick-connection device. Any quick connection device may be used, however, and the invention is by no means limited to the use of the configuration shown in FIGS. 14A and 14B.

Exemplary quick disconnect comprises a male component 140 (shown in FIG. 14A) attached to bobbin carrier base 142 and a female component 141 (shown in FIG. 14B), typically attached to the bobbin carrier footplate (not shown) that rides along the notch gears (not shown) of the braiding machine (not shown). Male component 140 comprises a cylindrical post 144 and a cylindrical pin 145 inserted perpendicular to and through the post. A helical spring 146 extends about post 144 from pin 145 to bobbin carrier base 142. The bobbin carrier (not shown) typically attaches to male component 140 on the surface (not shown) of bobbin carrier base 142 opposite post 144. Female component 141 comprises a base 148 having therein a cavity 147 having an X-shaped entryway 149 adapted to accept the post and the pin in one of two orientations. To connect male component 140 to female component 141, post 144 and pin 145 are inserted in cavity 149 and spring 146 is compressed while the male component is turned ⅛ of a full revolution such that the pin is positioned in accordance with indent 150 shown in dashed outline in FIG. 14B. Thus, the spring 146 biases pin 145 against indent 150 in the cavity wall such that the post and pin cannot rotate unless the spring is compressed further. The X-shape of the entryway 149 allows male component 140 to either be inserted and turned to the right or inserted and turned to the left, depending upon which side of the X the pin is inserted into. To disconnect the components, then, male component 140 may merely be manipulated to compress spring 146 and then turned 1/8 of a revolution either to the left or the right so that the pin can exit the cavity through the X-shaped entryway. In an exemplary construction, base 148 of female component 141 may comprise a block of metal machined to create cavity 149 and indent 150 and then attached to the bobbin carrier footplate, such as with screws 151.

Figure 5B:
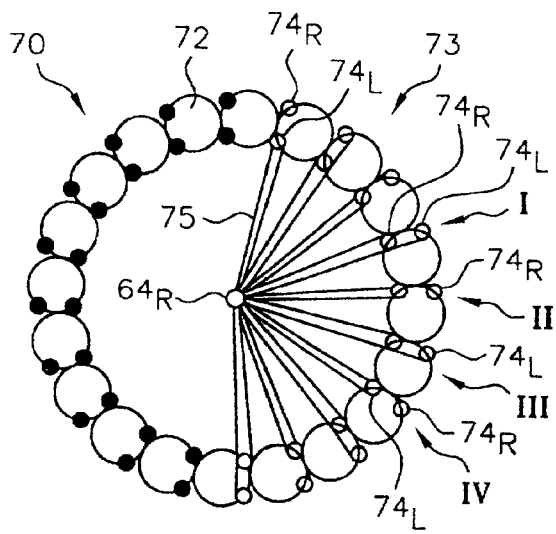
FIG. 5B is a front view of the notch gears in the braiding machine of FIG. 5A, with the first set of bobbins regrouped to the right side after forming the first leg section.

The bobbin regrouping process can be essentially understood by comparing FIGS. 5A and 5B. Prior to bobbin regrouping, the bobbins are configured as shown in FIG. 5A, with pairs of bobbins I, II, III, and IV positioned relative to one another as shown. To regroup the bobbins, pair III remains in place, and the remaining bobbins are moved such that there are no empty bobbin carriers between pairs of loaded bobbin carriers in the loaded portion of the circle of notch gears 72, as shown in FIG. 5B. Thus, pairs I, II, and IV move from the positions shown in FIG. 5A to the positions shown in FIG. 5B.

During the bobbin regrouping steps, it is desirable to preserve the clockwise or counter-clockwise rotation of each bobbin 74. Bobbin carriers 71L can be said to form a first set of bobbin carriers that traverse the circle of notch gears 72 in the counter-clockwise direction, whereas bobbin carriers 71R form a second set of bobbin carriers that traverse the circle in the clockwise direction. Thus, it may be desirable for bobbin 74L that rests on a bobbin carrier 71L before regrouping, to also reside on a bobbin carrier 71L after regrouping. Where the entire bobbin carrier is removed, it is desirable for the bobbin carrier to be replaced in a position where it travels in the same direction as it traveled prior to removal. Thus, for example when braiding with a 1:1 single filament braiding ratio in the legs and a 2:2 single filament braiding ratio (described herein later) in the trunk, bobbin 74 (or bobbin/bobbin carrier combination) on inner radius 78 may need to be switched with the bobbin (or bobbin/bobbin carrier combination) on outer radius 76 for every alternating pair of bobbins. Thus, for example, for pairs of bobbins I, II, III, and IV shown in FIG. 5A, where pair III stays in position and the remaining bobbins are regrouped together, pair III and pair I remain with bobbin 74L on outer radius 76 and bobbin 74R on inner radius 78, whereas pair II and pair IV switch bobbin 74L to inner radius 78 and bobbin 74R to outer radius 76. The counter rotation of the notch gears means that each notch gear 72 having a clockwise-rotating bobbin 74R on outer radius 76 has neighboring notch gears on either side with the clockwise-rotating bobbin on inner radius 78. In an alternate embodiment, bobbin carriers 71L (and therefore bobbins 74L) may travel clockwise instead of counter-clockwise, with carriers 71R and bobbins 74R travelling counter-clockwise. It may be preferable, however, for the tangent of the wire to the bobbin to be on the same side of the bobbin as on the mandrel so that the wire is wound on the same helical direction on the mandrel as it was on the bobbin. For example, as shown in FIG. 5A, the wire originating from bobbin 74R is tangent to the right side of both the bobbin and mandrel 64R, and likewise the wire originating from bobbin 74L is tangent to the left side of both the bobbin and mandrel.

Figure 7:
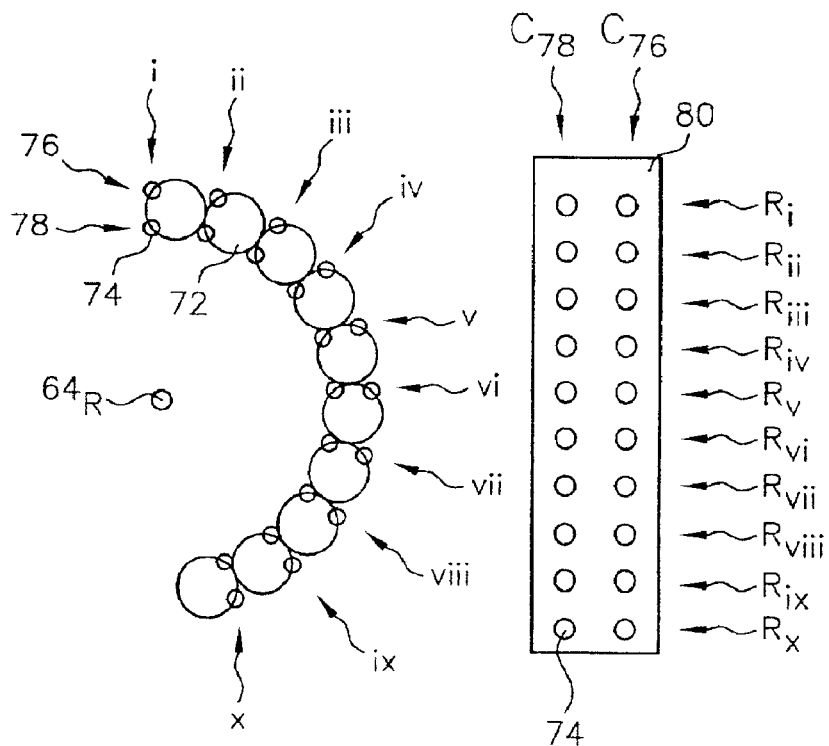
FIG. 7 is a front view of a portion of the notch gears in the braiding machine of FIG. 5A and a front view of a rack for holding bobbins removed from the machine.

After regrouping of the bobbins is complete, first portion 73 of the predetermined number of bobbins 74 is removed and put aside, along with the completed leg braid still on leg mandrel 64R. Referring now to FIG. 7, to facilitate removing (and later replacing) first portion 73 of bobbins 74, the bobbins (or bobbin carriers) may be stored on a rack 80 so that the bobbins maintain the correct orientation and do not get tangled while they are set aside. The rack may take any form, from a configuration that mimics the configuration of the circle of notch gears 72 to a linear configuration wherein each place for holding a bobbin is easily identified with a corresponding position in the circle. For example, as shown in FIG. 7, the rack may comprise a 10-row by 2-column array, columns $C_{76}$ and $C_{78}$ corresponding to outer radius 76 and inner radius 78 of machine 70, respectively, and rows $R_i$–$R_x$ corresponding to pairs of bobbins i–x on machine 70. Thus, the bobbin on outer radius 76 of pair i is placed on row $R_i$, column $C_{76}$ of rack 80, the bobbin on inner radius 78 of pair x is placed on row $R_x$, column $C_{78}$, and so on.

Figure 5C:
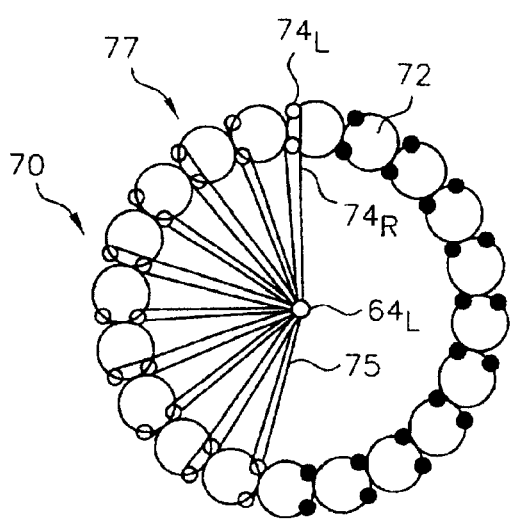
FIG. 5C is a front view of the notch gears in the braiding machine of FIG. 5A, with the second set of bobbins regrouped to the left side after forming the second leg section of the stent about the second leg mandrel.
Figure 5D:
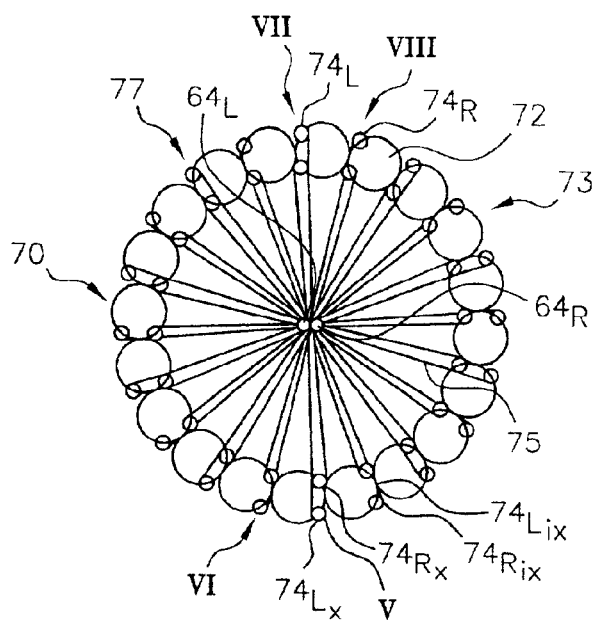
FIG. 5D is a front view of the notch gears in the braiding machine of FIG. 5C, shown fully loaded with both the first set and second set of bobbins and both leg mandrels.
Figure 5E:
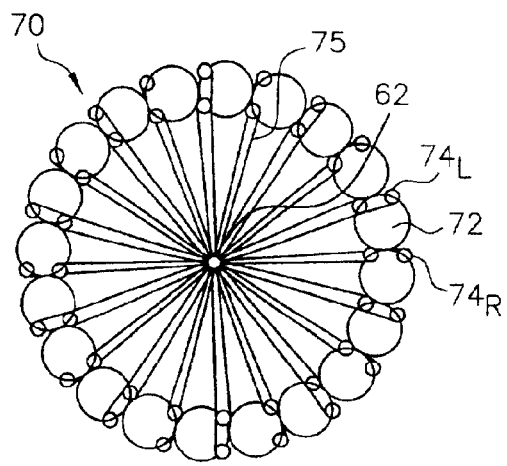
FIG. 5E is a front view of the notch gears in the braiding machine of FIG. 5D forming the braided trunk portion of the stent about the trunk mandrel that is connected to both leg mandrels.

A second leg is then braided about leg mandrel 64L with a second portion 77 of the predetermined number of bobbins 74 in the same manner as the first leg, except this time, after the leg has been braided, the second portion 77 is regrouped to the opposite side (the left side as shown in FIG. 5C) of the circle of notch gears 72. The first portion 73 of bobbins has a first discrete plurality of continuous filaments associated with it while the second portion 77 has a second discrete plurality of continuous filaments associated with it. Thus, each leg 54 and 56 is individually braided and comprises a discrete plurality of continuous filaments, such that each leg consists of filaments that are separate entities relative to the filaments of the other leg. After second portion 77 has been regrouped, first portion 73 is returned to the machine, and leg mandrel 64R and the braid thereon are positioned alongside the second leg mandrel 64L as shown in FIG. 5D. The two mandrels are then attached to trunk section mandrel 62 as shown in FIG. 5E. With first portion 73 returned to braiding machine 70, each bobbin carrier on the machine now has a bobbin mounted thereon. The braiding operation continues, now with all forty bobbins traversing the circle of notch gears 72 to create a braid around trunk section mandrel 62.

Although not shown, some of the filaments may be curtailed at the interface between the legs and the trunk portion, such that the trunk portion might consist of less than all of the filaments from the two portions 73 and 77. Conversely, the trunk portion may comprise more than all the filaments from the two portions 73 and 77. It is only necessary that at least one continuous filament from each discrete plurality of continuous filaments extend into the trunk portion, although it is preferred that at least half of each do so, and most preferred that all of them do so. Furthermore, portions 73 and 77 as illustrated herein each comprise half of the total number of bobbins. It may be desirable in certain applications, however, for one leg to have more filaments in it than the other, such as if one leg has a greater diameter than the other. In such a case, portions 73 and 77 may be unequal.

Rather than braiding a first leg, removing the bobbins, then braiding a second leg, bringing back in the removed bobbins, and then braiding the trunk section all on the same machine, a plurality of machines may be used. For example, a first machine may be used only for braiding leg sections. After each leg section is braided on the first machine, the bobbins may then be removed such as onto a rack as described above, and ported to a second machine. The second machine may be used for combining together two or more pre-braided leg sections.

Figure 8:
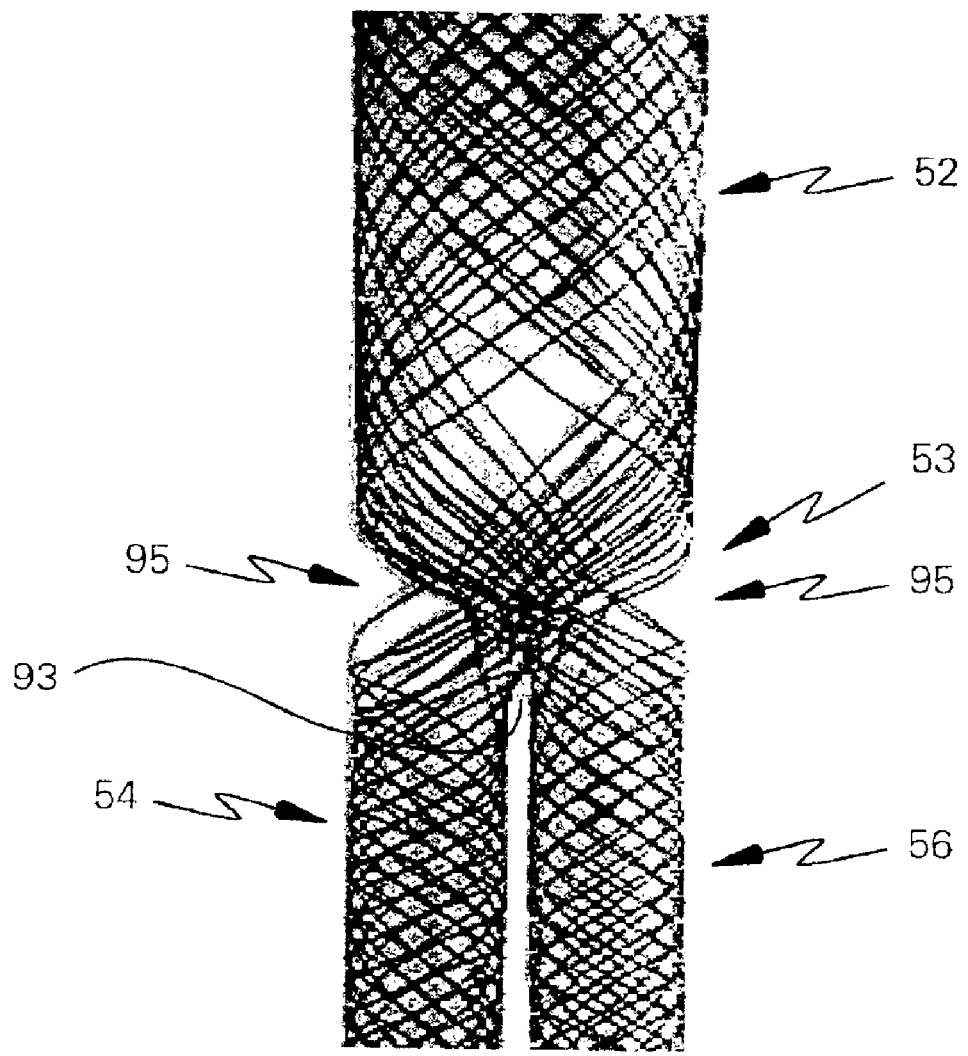
FIG. 8 is a front view of a portion of an exemplary stent embodiment having a closed crotch and open hips according to the present invention.

A variation on the above method may eliminate the step of regrouping the bobbins to one side of the circle of notch gears 72 before removing first portion 73 of the predetermined number of bobbins 74. In such case, first portion 73 is merely removed from the circle without regrouping, such as in the position shown in FIG. 5A, and stored. After braiding the second leg, second portion 77 of the predetermined number of bobbins 74 is then left in a spaced configuration similar to that shown in FIG. 5F, and the first portion 73 is merely inserted to fill the gaps between the second portion 77. Trunk section mandrel 62 is then attached to leg mandrels 64L and 64R and the winding continues as described above. This method produces a stent such as is shown in FIG. 8.

Figure 15B:
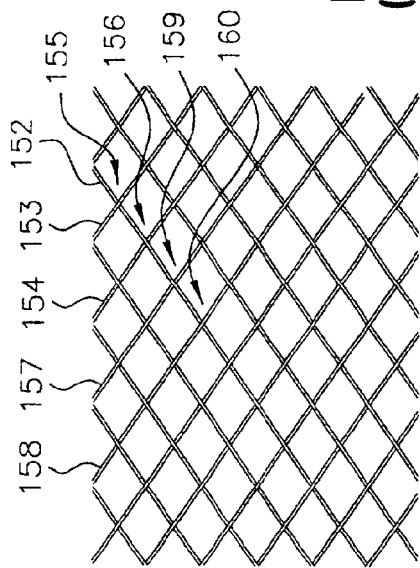
FIG. 15B depicts a portion of an exemplary stent embodiment having a 2:2 single filament braiding ratio as is known in the art, the stent having been cut longitudinally and flattened.

By either method described above for braiding about trunk section mandrel 62, the wires are braided in a 2:2 single filament braiding ratio with the machine at full capacity as shown in FIG. 5E. A 2:2 single filament braiding ratio is illustrated in FIG. 15B wherein, for example, following consecutive overlaps of single filament 152 wound in a first helical direction, the filament travels over two oppositely-wound filaments 153 and 154 at overlaps 155 and 156, respectively, and then travels under two filaments 157 and 158 at overlaps 159 and 160, respectively, and so on. This is true of each filament in the braid. FIG. 15A illustrates a 1:1 single filament braiding ratio, wherein following consecutive overlaps of filament 161 wound in a first helical direction, the single filament travels over one oppositely-wound filament 162 at overlap 163 and then travels under filament 164 at overlap 165, and so on. The stent may be manufactured using braiding machines having a different number of notch gears or using a different percentage of the capacity when winding, thus allowing preparation of stents having a 1:1 single filament braiding ratio throughout, a 1:1 paired filament braiding ratio as shown in FIG. 15C and described below, or other configurations as desired. The exact braiding configuration, however, is not intended as a limitation upon this invention. Furthermore, the illustrations in FIGS. 15A–C are intended only to depict the general braiding configurations of the filaments in relation to one another, and do not necessarily represent the actual number of filaments or the precise look of an actual stent.

Figure 16:
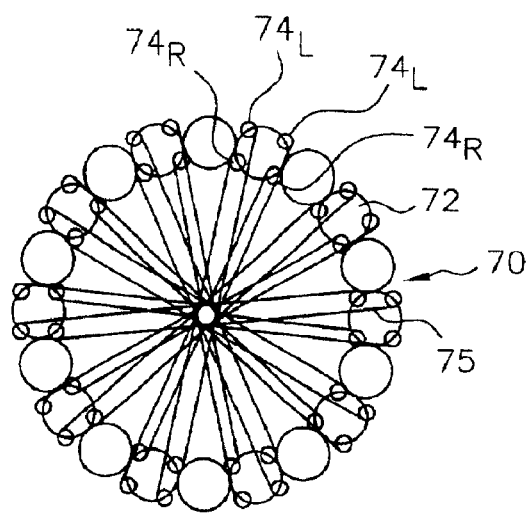
FIG. 16 is a front view of the notch gears of a braiding machine, loaded with a set of wire bobbins in 1:1-in-train configuration that produces a 1:1 paired filament braiding ratio, as is known in the art.

A 1:1 paired filament braiding ratio can be achieved by positioning the bobbin carriers on the notch gears in such a way that the bobbins traveling in the same helical direction travel in pairs such that no bobbin traveling in the opposite direction crosses in-between the pairs. This particular bobbin carrier configuration for achieving a 1:1 paired filament braiding ratio may also be referred to as "1:1-in-train" configuration, referring to how the bobbin pair travel together as if linked in a train. Such a positioning is shown in FIG. 16, where bobbins 74L proceed about the circle counterclockwise and bobbins 74R proceed clockwise.

Figure 9:
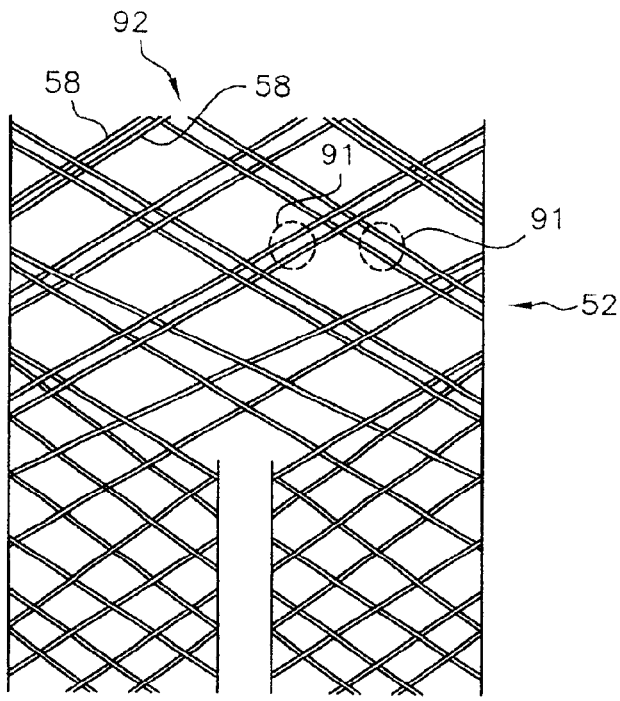
FIG. 9 is a front view illustration of an exemplary stent embodiment having legs in a 1:1 single filament braiding ratio and the body in a 1:1 paired filament braiding ratio according to the present invention.
Figure 10A:
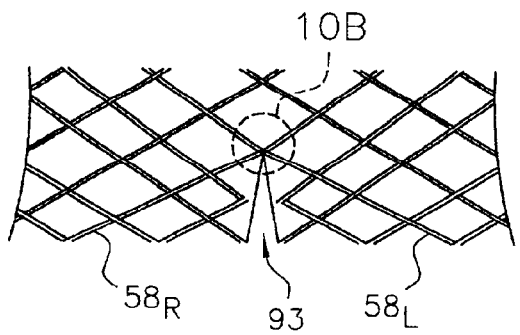
FIG. 10A is a front view illustration of a portion of an exemplary stent embodiment having a closed crotch and closed hips according to the present invention.

Referring now to FIG. 9, this method may be used, for example, to produce a stent 92 having a body section 52 with a 1:1 paired filament braiding ratio. The 1:1 paired filament braiding ratio is also shown in FIG. 15C. As shown in FIG. 15C, following a pair of filaments 166 and 167 wound in a first helical direction through consecutive overlaps, the pair travels together over a pair of oppositely-wound filaments 168 and 169 at overlap 170 and then travels under another pair of oppositely-wound filaments 171 and 172 at overlap 173.

Figure 5F:
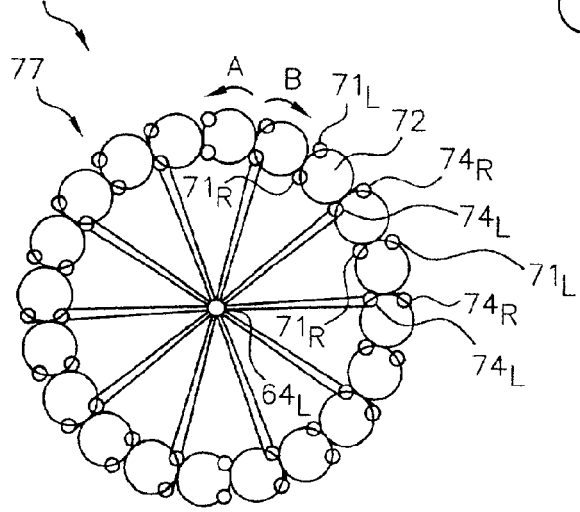
FIG. 5F is a front view of the notch gears in the braiding machine of FIG. 5A in an alternative embodiment wherein the second set of bobbins is not regrouped to the left side prior to adding back in the first set of bobbins.

In an alternative embodiment for achieving a 1:1 paired filament braiding ratio, each bobbin carrier 71 may be adapted to hold two bobbins. The body of the stent may be braided with the bobbins grouped two bobbins to a single carrier, whereas the legs are braided with the bobbins distributed with only a single bobbin per each occupied carrier. This configuration for braiding the body appears similar to FIG. 5A or 5F from above, except that each bobbin as shown represents two bobbins 74 stacked one on top of another. The stacked configuration can be derived essentially by first grouping the bobbins as shown in FIG. 5D and then consolidating, for example, bobbin $74L_{ix}$ on top of $74L_x$ and bobbin $74R_{ix}$ on top of $74R_x$ and so on around the circle, so that the resulting configuration resembles the configuration in FIG. 5F but with two bobbins stacked one on top of the other. The result is that each carrier in each set of carriers having a common direction of rotation having two bobbins thereon is surrounded on both sides by empty carriers, such as for example, carrier 74L having empty carriers 71L on either side as shown in FIG. 5F. Similarly, each pair of loaded carriers having two bobbins apiece has an empty carrier therebetween, such as for example, carriers 74R having empty carrier 71R therebetween as shown in FIG. 5F.

The braided bifurcated stent may also be constructed by processes that are essentially the reverse of those described above. By such processes, the braiding begins about trunk section mandrel 62 with the full capacity of bobbins as shown in FIG. 5E, and then one portion of the bobbins 74 are removed from the machine and set aside while one leg of the stent is braided about a leg mandrel using the remaining portion of the bobbins. For example, first portion 73 may be removed while second portion 77 forms a braid about mandrel 64L as shown in FIG. 5C. After the trunk section and one leg of the stent have been created with one portion of the bobbins, that portion is removed and the other portion is returned to the machine so that the other leg can be braided about the other leg mandrel. Thus, second portion 77 may be removed and first portion 73 replaced in the machine to form a braid about mandrel 64R as shown in FIG. 5B. Similar to the process wherein the legs are braided first, the full set of bobbins can be split to make the legs such that all the bobbins on one portion are used for one leg and all the bobbins on the other portion are used for the other leg, such as is shown in FIGS. 5B and 5C, or the bobbins used to braid one side and the bobbins used to braid the other side may comprise alternating pairs prior to being split, such as is shown in FIGS. 5A and 5F. Because one leg must be braided first and then the other leg must be braided in a position parallel to that leg, leg mandrel 64 must be removed and the first-created leg bent back out of the path of braiding zone 90 during creation of the second-created leg. Similarly, during creation of the first-created leg, the set of bobbins 74 and wires 75 connected thereto for creation of the second-created leg and extending from the trunk section of the stent must be pulled into a position that does not interfere with the braiding of the first-created leg.

Depending on the method of grouping the bobbins when converting from braiding the legs to braiding the body, or vice versa, crotch region 93 of the stent may be open or closed. The method wherein the bobbins are grouped such that the bobbins from one leg are grouped on one side of the machine and the bobbins from the other leg are grouped on the other side of the machine as shown in FIG. 5D, produces a stent with an open crotch 93 such as is shown in FIG. 3. An EVG constructed using a braided stent having an open crotch thus has an unsupported bifurcation septum. That is, the graft may not have underlying stent structure in the area where the graft bifurcates into the two legs. This may provide certain advantages, such as elimination of any graft-stent wear in that particular region, which is a region that may be subjected to more movement than other portions of the stent, and thus likely to provide more such wear in other designs.

Figure 11A:
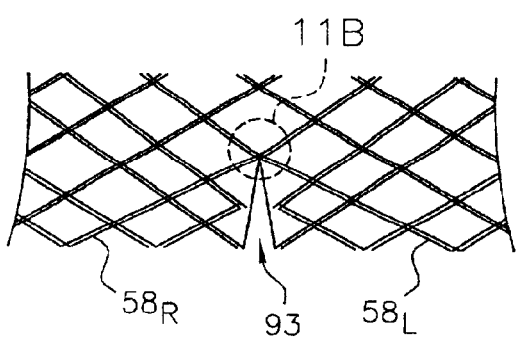
FIG. 11A is a front view illustration of a portion of another exemplary stent embodiment having a closed crotch and closed hips according to the present invention.
Figure 10B:
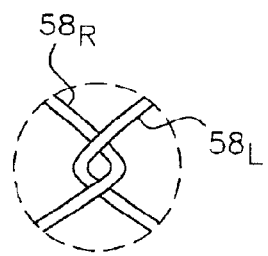
FIG. 10B is a front view of an enlarged portion of the stent of FIG. 10A, showing interlocked filaments from each leg providing closure for the crotch.
Figure 11B:
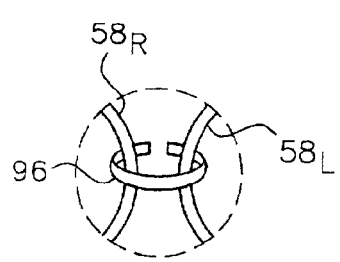
FIG. 11B is a front view of an enlarged portion of the exemplary stent of FIG. 11A, showing a staple providing closure for the crotch.

The method wherein the bobbins from each leg are alternated with the bobbins from the other leg as described with respect to FIG. 5F, produces a stent with a closed, woven crotch 93 and open hips 95, such as are shown in FIG. 8. To provide a closed crotch for the design shown in FIG. 3, one or more filaments from the adjacent legs may be crossed in crotch region 93 as illustrated in the enlarged view in FIG. 10B. Other configurations for closing crotch 93 with crossing filaments may be provided, such as by switching bobbins from one carrier to another as desired to produce different degrees of interwinding. Referring now to FIGS. 11A and 11B, it may be desirable to group certain of the braided filaments 58 together, in particular filaments from opposite legs in crotch region 93, using staples or sutures 96 to provide additional structure.

Figure 12:
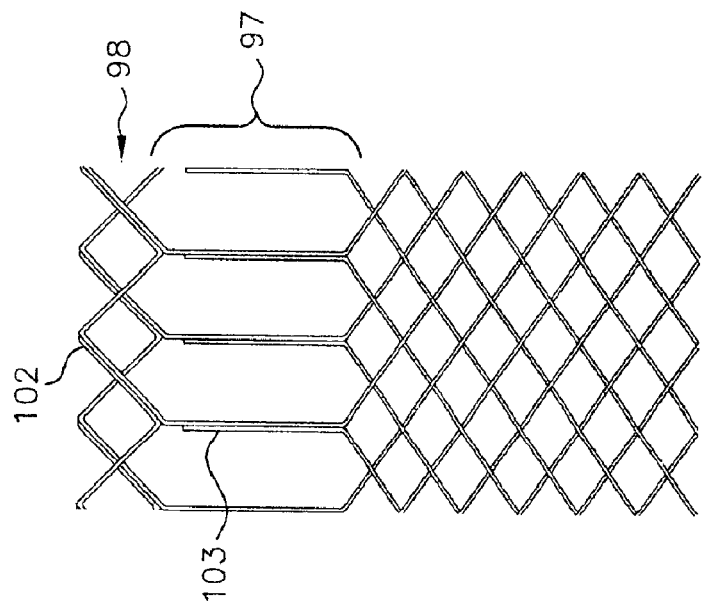
FIG. 12 depicts an end portion of an exemplary stent embodiment having an atraumatic end winding, the stent having been cut longitudinally and flattened.

To provide increased radial strength at the ends of the braided stent of this invention or to counteract a known end-effect of braided stent architecture wherein the ends tend to have lesser radial strength than the intermediate portion of the stent, the ends may be flared as is well known in the art, or the ends may comprise a non-braided stent architecture such as is shown in FIG. 12. The structure and method for making a hexagonal non-braided architecture 97 with an overlapping zig-zag end winding 98 shown in FIG. 12 is disclosed fully in pending U.S. patent application Ser. No. 09/442,165 by the common inventors Chouinard and Haverkost of this invention, filed on Nov. 17, 1999, assigned to the common assignee, and incorporated herein by reference. Consistent with the disclosure in the '165 Application, a stent according to the present invention having a braided crotch region may have a non-braided architecture in any portion of the stent other than in the crotch. For example, in one embodiment every region except the crotch region may have a non-braided architecture. Other embodiments may include non-braided architecture in any region of the stent where additional radial strength is desired, such as between two braided regions. Yet another embodiment may have a non-braided architecture at every end on both the distal (furthest from the position outside the lumen from which the stent is introduced) and proximal (nearest to the position outside the lumen from which the stent is introduced) ends of the stent, or on only selected ends of the stent, such as only on the upstream end or ends. The end architecture is not limited to the architecture shown and described above, but may comprise any number of configurations known in the art. If desired, a separate stent having greater radial strength may be deployed to overlap one or more of the ends, as is also known in the art.

Another method for developing a greater radial strength in one section of the stent relative to another comprises using a tapered wire to form the stent. For example, the wire can taper from a first, relatively smaller diameter or cross-sectional area used for braiding leg sections 54 and 56, for example, to a second, relatively larger diameter or cross-sectional area used for braiding body 52. Thus, body 52 may have a greater radial strength than otherwise provided by a single wire diameter throughout. The taper may also be reversed to provide greater radial strength in the legs, if desired. This tapering may also be applied to non-bifurcated, braided stent designs. The use of a continuous wire having regions of different cross-sectional area for providing variable stiffness in different regions of a stent is generally discussed in U.S. application Ser. No. 09/442,192 to Zarbatany et al., incorporated herein by reference.

Figure 17:
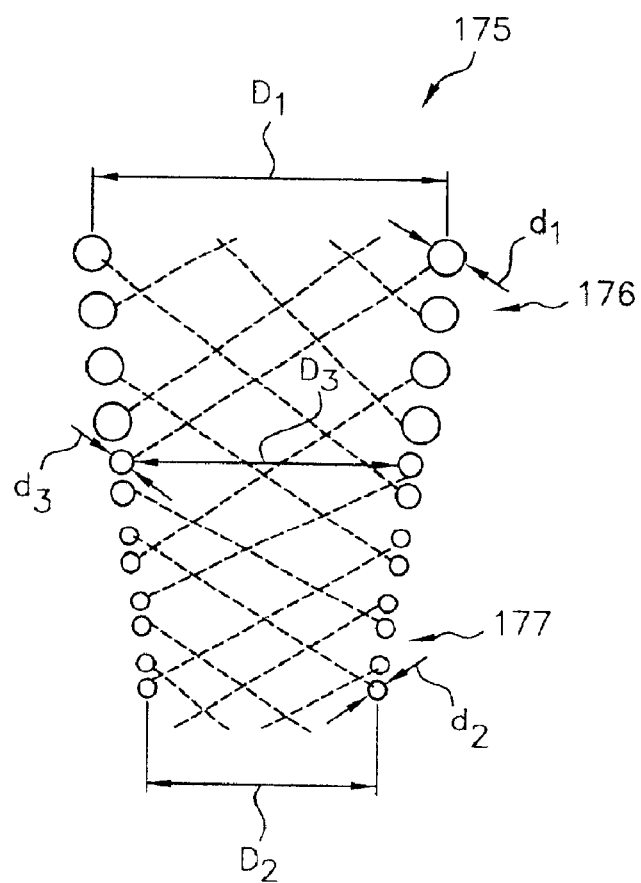
FIG. 17 is a cross-sectional view of an exemplary stent according to the present invention comprising tapered filaments.

Tapered filaments may be used on any braided stent, not just on a bifurcated stent. All of the plurality of continuous filaments may be tapered filaments, or only a fraction of the filaments. In a non-bifurcated stent, one end portion of the braided stent may comprise the larger cross-section ends of all the tapered filaments and the other end portion of the stent may comprise the smaller cross-section ends of all the tapered filaments. As used herein in connection with the braided stent, the "end portion" may comprise only a short portion, such as a single row of overlaps that includes the end of the stent, or may include a larger portion, such as one half or more of the stent that includes the end. One example of such a non-bifurcated stent comprising tapered wire is shown in FIG. 17. Stent 175 comprises a distal end portion 176 and a proximal end portion 177. The distal end portion has a larger stent diameter D1 and the proximal end portion has a smaller stent diameter D2. In certain applications, it may be desirable for the larger diameter portion of the stent to comprise a larger diameter filament than the filament, diameter in the smaller diameter portion. Thus, as shown, each filament may have a diameter d1 in the larger diameter portion of the stent and a smaller diameter d2 in the smaller diameter portion of the stent. Furthermore, both the stent and the wire may gradually taper, such that intermediate diameters D3 and d3 are present in the region between diameters D1 and D2. In other embodiments, the diameter of the wire may taper less gradually, such that the change in wire diameter along the stent is more in the nature of a step-change. In one exemplary embodiment, for example, D1 may equal about 24 mm and D2 may equal about 12 mm, with d1 equal to about 0.355 mm and d2 equal to about 0.255 mm. Any variety of dimensions may be used. In some applications D1 may equal D2, with only d1 and d2 being varied along the length of the stent.

The tapered-filament stent may comprise any combination of end windings or braiding ratios discussed herein or known in the art. The tapered-filament stent may be configured in any way desired for placement in a lumen, such as tapering from one end to the other as shown in FIG. 17, or with a smaller diameter in the middle than in the ends, or vice versa, or merely a single diameter throughout. All of the wires in the braided stent may be tapered, or only some fraction of the wires. The filament may have multiple tapers, such as from a larger diameter at one end, to a smaller diameter in the middle, to a larger diameter at the other end, or vice versa. The smaller diameter section of the filament may be positioned such that is coincides with a tortuous portion of a lumen requiring greater flexibility than other regions of the stent. Although described herein with reference to a larger or smaller diameter, the wire may have a non-round cross-section, in which case the wire may taper from a relatively larger cross-sectional area to a relatively smaller cross-sectional area.

The end architecture as shown in FIG. 12 can be described as "atraumatic" in the sense that there are no loose wire ends that may puncture or irritate (cause trauma to) the lumen wall after implantation. Other methods of providing atraumatic ends may also be used as are known in the art. In particular, the stent may comprise, rather than, for example, ten filaments wound onto ten bobbins, five continuous filaments each having a first end wound onto a first bobbin and a second end wound onto a second bobbin, thus still having ten bobbins in all. The filaments can be positioned on the braiding machine with the midpoint of the filament making a loop around, for example, a radially protruding pin secured in the mandrel, and the first and second bobbins positioned on bobbin carriers in positions consistent with the helical angle of the stent and the distance of the mandrel from the bobbin carriers. Thus, the first and second bobbins may be positioned at opposite ends of a radius of the circle of notch gears, or at opposite ends of some chord through the circle, depending on the exact configuration of the machine and desired helical angle of the stent. An exemplary process for providing a stent with such ends is described in publication WO 99/25271 to Burlakov et al. and is incorporated herein by reference.

Figure 13B:
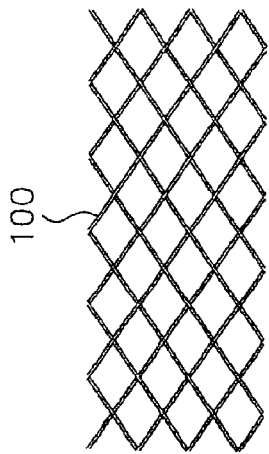
FIG. 13B depicts an end portion of an exemplary stent embodiment having ends that terminate freely at the end of the stent as is known in the art, the stent having been cut longitudinally and flattened.
Figure 13D:
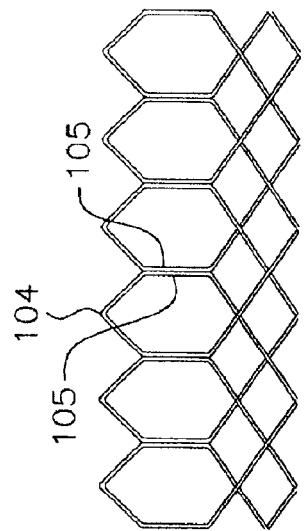
FIG. 13D depicts an end portion of an exemplary stent embodiment having ends that terminate in a non-braided configuration with continuous apices at the end of the stent, the stent having been cut longitudinally and flattened.
Figure 13A:
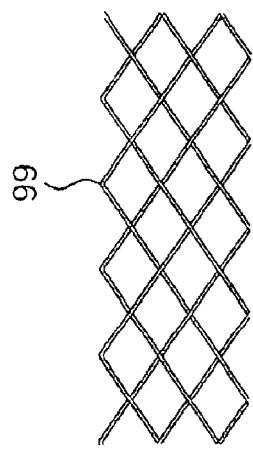
FIG. 13A depicts an end portion of an exemplary stent embodiment having continuous apices at the end of the stent as is known in the art, the stent having been cut longitudinally and flattened.
Figure 13C:
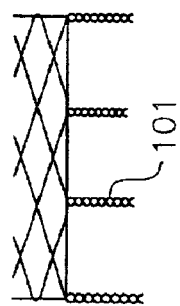
FIG. 13C depicts an end portion of an exemplary stent embodiment having ends that terminate in a twisted configuration at the end of the stent as is known in the art, the stent having been cut longitudinally and flattened.

Thus, using the method described above, one end of the stent has continuous-wire apices 99 such as are shown in FIG. 13A at one end. The filaments on the opposite ends may be freely terminating ends 100, such as are shown in FIG. 13B; twisted together ends 101, such as are shown in FIG. 13C and in publication WO 99/25271; or atraumatically disposed ends in a non-braided architecture, such as for example in positions 102 and 103 as shown in FIG. 12 and further discussed in U.S. patent application Ser. No. 09/442,165. These are only examples, however, as the free ends may terminate in any way known in the art. Although one end of a stent may have some combination of continuous-wire apices 99 and otherwise-terminated free ends 100, 101, or 102 and 103, the preferred embodiment comprises one end of the stent having only continuous-wire apices 99. It should also be understood that because the braiding process proceeds from one end of the stent to the other, typically either the body end comprises continuous-wire apices 99 and the leg ends comprise otherwise-terminated free ends 100, 101, or 102 and 103, or the leg ends comprise all continuous-wire apices and the body end comprises all otherwise-terminated free ends. All or only some of the leg ends may comprise continuous-wire apices.

The above method for providing continuous-wire apices at one end may also be combined with the use of tapered wire as described herein. For example, a wire having multiple tapers with a relatively smaller diameter in a middle region of the wire and a relatively larger diameter in the opposite end regions, may be wound onto two bobbins. The relatively smaller diameter wire may be, for example, wound about a protruding pin at the midpoint of the wire, and the each leg region braided as described herein. The trunk region may then be braided as described herein, with the taper in the wire diameter located such that the trunk has a relatively larger diameter wire than each of the legs. The wire may comprise only the first diameter at the opposite ends and the second diameter in the middle, with a gradual taper between regions, or the wire may comprise a third diameter intermediate the end and middle diameters for use in the bifurcated region.

The use of continuous-wire apices at one end may be further combined with the configurations described in U.S. patent application Ser. No. 09/442,165, wherein one or more regions of the stent may comprise a non-braided configuration. Thus, for example, the midpoint of a wire, such as a tapered wire, may be positioned at a non-braided end of a stent, creating continuous apices 104 such as are shown in FIG. 13D. The non-braided architecture may be created, for example, by winding the wire about pins on a mandrel as is well known in the art, and then once the non-braided section has been formed, braiding the remainder of the stent about the mandrel as described herein. The parallel wire sections 105 in the non-braided portion may be optionally welded together prior to braiding the remainder of the stent.

The above combinations may also be used with a non-bifurcated, braided stent. For example, a braided, non-bifurcated stent may comprise tapered filaments wherein the ends of the stent comprise larger cross-sectional area regions of the tapered filaments and the middle of the stent comprises the smaller cross-sectional area regions of the tapered filaments. Conversely, the smaller cross-sectional area regions may be on the ends and the larger cross-sectional area in the middle. As the larger cross-sectional area wire tends to provide greater stiffness or greater radial strength or both, the larger cross-sectional wire may be used in any region of the stent desired to have increased stiffness and radial strength relative to the rest of the stent, or may be used in certain regions to counteract influences which otherwise would result in lesser stiffness or lesser radial strength in such regions. Atraumatic end windings, such as the continuous-wire apices described herein and with reference to Publication WO 99/25271 and the various configurations as described herein with reference to U.S. patent application Ser. No. 09/442,165, may also be used in conjunction with tapered filaments in such braided, non-bifurcated stents. Such end windings may also be used in non-bifurcated stents without tapered filaments.

To deploy the stent of this invention, the stent is typically compressed into a radially compressed state into an introducer as is well-known in the art. The stent is then introduced to the lumen into which it is to be deployed, navigated through the lumen to a deployment location, typically a diseased artery such as the aorta, and then expanded to a radially expanded state in the deployment location as is known in the art. The deployment of a unitary stent of the present invention is thus deployed by a method similar to that used for any unitary bifurcated stent known in the art, and the deployment of a modular stent according to the present invention is thus deployed by a method similar to that used for any modular bifurcated stent known in the art.

Although bifurcated stent designs have been shown and described herein, the method of the present invention may be used for creating a stent that branches into any number of multiple lumen, so long as there are a sufficient number of bobbins available in the braiding machine to provide an adequate number of wires for braiding the branch sections. To the extent that existing braiding machines may not have a sufficient number of bobbins, machines with a greater number of bobbins may be designed without departing from the scope of this invention.

Although illustrated and described above with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A process for constructing a braided, branched stent having a body and a plurality of legs, each leg comprising a discrete plurality of continuous filaments, the process comprising the steps of:
   a) braiding each plurality of continuous filaments to individually form at least first leg portions of each of the legs;
   b) braiding at least one filament from each plurality of continuous filaments together to form a first body portion of the body; and
   c) configuring at least a fraction of one plurality of leg filaments into a non-braided configuration in a second portion of the leg, configuring at least a fraction of each plurality of leg filaments into a non-braided configuration in a second portion of the body, or a combination thereof.

2. The process of claim 1 wherein the plurality of legs comprises a first leg and a second leg and step (a) comprises the steps of:
   i) braiding a first discrete plurality of filaments to form the first leg; and ii) braiding a second discrete plurality of filaments to form the second leg; and step (b) comprises braiding the first plurality of filaments and the second plurality of filaments together to form the body.

3. The process of claim 2 wherein step (a) is performed prior to step (b).

4. The process of claim 2 comprising braiding the stent around a mandrel having a mandrel body, a first detachable mandrel leg, and a second detachable mandrel leg, wherein step (a)(i) comprises braiding the first plurality of filaments about the first detachable mandrel leg, step (a)(ii) comprises braiding the second plurality of filaments about the second detachable mandrel leg, and step (b) comprises braiding the first plurality of filaments and second plurality of filaments together about the mandrel body.

5. The process of claim 4 comprising performing the braiding on a braiding machine having a predetermined plurality of bobbins adapted to revolve in a pattern about a longitudinal axis, a first set of bobbins adapted to revolve in a first circumferential direction and a second set of bobbins adapted to revolve in a second circumferential direction, each bobbin mounted upon a bobbin carrier adapted to carry at least one bobbin, each bobbin adapted to provide one or more filaments for braiding within the stent, step (a) comprising in step (i) using filaments from a first portion of the predetermined plurality of bobbins to braid the first leg about the first detachable mandrel leg positioned substantially along the longitudinal axis in a braiding zone, the braiding zone being a conical zone defined by the filaments extending from the bobbins to the stent on the mandrel, and in step (ii) using filaments from a second portion of the predetermined plurality of bobbins to braid the second leg about the second detachable mandrel leg positioned in the braiding zone; and step (b) comprising using filaments from both portions of the predetermined plurality of bobbins to braid the body about the mandrel body positioned in the braiding zone.

6. The process of claim 5 further comprising the steps of:
A) first performing step (a)(i);
B) then removing the first portion of the predetermined plurality of bobbins from the braiding machine and removing the first mandrel leg from the braiding zone;
C) then performing step (a)(ii);
D) then returning the first portion of the predetermined plurality of bobbins to the braiding machine, attaching the first mandrel leg and the second mandrel leg to the mandrel body, and positioning the mandrel body in the braiding zone; and
E) then performing step (b).

7. The process of claim 6 wherein prior to removing the first portion of the predetermined plurality of bobbins from the machine, the process further comprises grouping the first portion of the predetermined plurality of bobbins on a first side of the machine; and prior to returning the first portion of the predetermined plurality of bobbins to the first side of the machine, the process further comprises grouping the second portion of the predetermined plurality of bobbins onto a second side of the machine.

8. The process of claim 5 comprising prior to steps (a) and (b), winding the filaments between two bobbins such that a first end of the filament is wound on a first bobbin and a second end of the filament is wound on a second bobbin, and positioning a midpoint of the filament on the mandrel to form an apex at an end of the stent.

9. The process of claim 1 wherein step (a) is performed on a first braiding machine and step (b) is performed on a second braiding machine.

10. A process for constructing a braided, branched stent having a body and a plurality of legs, each leg comprising a discrete plurality of continuous filaments, the process comprising the steps of:
a) braiding each plurality of filaments to individually form at least first leg portions of each of the legs; and
b) braiding at least one filament from each plurality of continuous filaments together to form a first body portion of the body;
wherein step (b) is performed prior to step (a).

11. The process of claim 10 wherein each leg and the body have respective lengths and the process further comprises braiding the plurality of filaments in each leg over the entire length of each leg and braiding all of the filaments of each plurality of leg filaments together in the body over the entire length of the body.

12. The process of claim 10 further comprising one of: configuring at least a fraction of one plurality of leg filaments into a non-braided configuration in a second portion of the leg, configuring at least a fraction of each plurality of leg filaments into a non-braided configuration in a second portion of the body, or a combination thereof.

13. A process for constructing a braided, branched stent using a braiding machine having a predetermined plurality of bobbins adapted to revolve in a pattern about a longitudinal axis, a first set of bobbins adapted to revolve in a first circumferential direction and a second set of bobbins adapted to revolve in a second circumferential direction, each bobbin mounted upon a bobbin carrier adapted to carry at least one bobbin, each bobbin adapted to provide one or more filaments for braiding within the stent, the stent having a body and a plurality of legs, each leg comprising a discrete plurality of continuous filaments, the process comprising braiding the stent around a mandrel having a mandrel body, a first detachable mandrel lea, and a second detachable mandrel leg, the process comprising the steps of:
(a)(i) braiding a first discrete plurality of continuous filaments to individually form at least first leg portions of a first leg, using filaments from a first portion of the predetermined plurality of bobbins to braid the first leg about the first detachable mandrel leg positioned substantially along the longitudinal axis in a braiding zone, the braiding zone comprising a conical zone defined by the filaments extending from the bobbins to the stent on the mandrel;
(a)(ii) braiding a second discrete plurality of continuous filaments to individually form at least first leg portions of a second leg, using filaments from a second portion of the predetermined plurality of bobbins to braid the second leg about the second detachable mandrel leg positioned in the braiding zone;
(b) braiding the first plurality of continuous filaments and the second plurality of continuous filaments together to form a first body portion of the body, using filaments from both portions of the predetermined plurality of bobbins to braid the body about the mandrel body positioned in the braiding zone;
wherein the process comprising a sequence comprising:
A) first performing step (a)(i);
B) then removing the first portion of the predetermined plurality of bobbins from the braiding machine, and removing the first mandrel leg from the braiding zone;
C) then performing step (a)(ii);
D) then returning the first portion of the predetermined plurality of bobbins to the braiding machine, attaching the first mandrel leg and the second mandrel leg to the mandrel body, and positioning the mandrel body in the braiding zone; and E) then performing step (b);

wherein prior to removing the first portion of the predetermined plurality of bobbins from the machine, the process further comprises grouping the first portion of the predetermined plurality of bobbins on a first side of the machine; and prior to returning the first portion of the predetermined plurality of bobbins to the first side of the machine, the process further comprises grouping the second portion of the predetermined plurality of bobbins onto a second side of the machine; and wherein after or during the step of returning the first portion of the predetermined plurality of bobbins to the machine in step D, the process further comprises the steps of:

D1) identifying at least one adjacent pair of bobbins comprising a first bobbin from the first portion of the predetermined plurality of bobbins and a second bobbin from the second portion of the predetermined plurality of bobbins; and D2) crossing the filaments attached to the first and second bobbins so that the first leg and the second leg of the stent are interlocked together by the crossed filaments.

14. A process for constructing a braided, branched stent using a braiding machine having a predetermined plurality of bobbins adapted to revolve in a pattern about a longitudinal axis, a first set of bobbins adapted to revolve in a first circumferential direction and a second set of bobbins adapted to revolve in a second circumferential direction, each bobbin mounted upon a bobbin carrier adapted to carry at least one bobbin, each bobbin adapted to provide one or more filaments for braiding within the stent, the stent having a body and a plurality of legs, each leg comprising a discrete plurality of continuous filaments, the process comprising braiding the stent around a mandrel having a mandrel body, a first detachable mandrel leg, and a second detachable mandrel leg, the process comprising the steps of:

(a)(i) braiding a first discrete plurality of continuous filaments to individually form at least first leg portions of a first leg, using filaments from a first portion of the predetermined plurality of bobbins to braid the first leg about the first detachable mandrel leg positioned substantially along the longitudinal axis in a braiding zone, the braiding zone comprising a conical zone defined by the filaments extending from the bobbins to the stent on the mandrel;

(a)(ii) braiding a second discrete plurality of continuous filaments to individually form at least first leg portions of a second leg, using filaments from a second portion of the predetermined plurality of bobbins to braid the second leg about the second detachable mandrel leg positioned in the braiding zone;

(b) braiding the first plurality of continuous filaments and the second plurality of continuous filaments together to form a first body portion of the body, using filaments from both portions of the predetermined plurality of bobbins to braid the body about the mandrel body positioned in the braiding zone;

wherein the process comprising a sequence comprising:

A) first performing step (a)(i);

B) then removing the first portion of the predetermined plurality of bobbins from the braiding machine, and removing the first mandrel leg from the braiding zone;

C) then performing step (a)(ii);

D) then returning the first portion of the predetermined plurality of bobbins to the braiding machine, attaching the first mandrel leg and the second mandrel leg to the mandrel body, and positioning the mandrel body in the braiding zone; and E) then performing step (b);

wherein the step of returning the first portion of the predetermined plurality of bobbins to the machine in step D comprises placing each bobbin from the first portion of the predetermined plurality of bobbins in a position located circumferentially between two bobbins from the second portion of the predetermined plurality of bobbins.

15. A process for constructing a braided, branched stent using a braiding machine having a predetermined plurality of bobbins adapted to revolve in a pattern about a longitudinal axis, a first set of bobbins adapted to revolve in a first circumferential direction and a second set of bobbins adapted to revolve in a second circumferential direction, each bobbin mounted upon a bobbin carrier adapted to carry at least one bobbin, each bobbin adapted to provide one or more filaments for braiding within the stent, the stent having a body and a plurality of legs, each leg comprising a discrete plurality of continuous filaments, the process comprising braiding the stent around a mandrel having a mandrel body, a first detachable mandrel leg, and a second detachable mandrel leg, the process comprising the steps of:

(a)(i) braiding a first discrete plurality of continuous filaments to individually form at least first leg portions of a first leg, using filaments from a first portion of the predetermined plurality of bobbins to braid the first leg about the first detachable mandrel leg positioned substantially along the longitudinal axis in a braiding zone, the braiding zone comprising a conical zone defined by the filaments extending from the bobbins to the stent on the mandrel;

(a)(ii) braiding a second discrete plurality of continuous filaments to individually form at least first leg portions of a second leg, using filaments from a second portion of the predetermined plurality of bobbins to braid the second leg about the second detachable mandrel leg positioned in the braiding zone;

(b) braiding the first plurality of continuous filaments and the second plurality of continuous filaments together to form a first body portion of the body, using filaments from both portions of the predetermined plurality of bobbins to braid the body about the mandrel body positioned in the braiding zone;

wherein the process comprising a sequence comprising:

A) first performing step (b);

B) then removing the second portion of the predetermined plurality of bobbins from the machine and attaching the first mandrel leg to the mandrel body;

C) then performing step (a)(i);

D) then returning the second portion of the predetermined plurality of bobbins to the machine and removing the first portion of the predetermined plurality of bobbins from the machine, attaching the second mandrel leg to the mandrel body, detaching the first mandrel leg from the mandrel body, and positioning the first leg of the stent outside the braiding zone so that the first leg does not interfere with performance of step (a)(ii); and E) then performing step (a)(ii).

16. The process of claim 15 comprising designating the second portion of the predetermined plurality of bobbins to be removed from the machine in step B as all of the bobbins on one side of the machine.

17. The process of claim 16 comprising designating the first and second portions of the predetermined plurality of bobbins as alternating bobbins of each set of bobbin carriers such that in each set, each bobbin from the first portion is positioned on a bobbin carrier circumferentially between two bobbins from the second portion at a step in the process immediately prior to removal of the second portion from the machine in step B.

18. The process of claim 16 wherein prior to removing the second portion of the predetermined plurality of bobbins in step B, the process further comprises the steps of:
   B1) identifying at least one adjacent pair of bobbins comprising a first bobbin from the first portion of the predetermined plurality of bobbins and a second bobbin from the second portion of the predetermined plurality of bobbins; and
   B2) crossing the filaments attached to the first and second bobbins so that the first leg and the second leg of the stent are interlocked together by the crossed filaments.

19. A process for constructing a braided, branched stent using a braiding machine having a predetermined plurality of bobbins adapted to revolve in a pattern about a longitudinal axis, a first set of bobbins adapted to revolve in a first circumferential direction and a second set of bobbins adapted to revolve in a second circumferential direction, each bobbin mounted upon a bobbin carrier adapted to carry at least one bobbin, each bobbin adapted to provide one or more filaments for braiding within the stent, the stent having a body and a plurality of legs, each leg comprising a discrete plurality of continuous filaments, the process comprising braiding the stent around a mandrel having a mandrel body, a first detachable mandrel leg, and a second detachable mandrel leg, the process comprising the steps of:
   (a)(i) braiding a first discrete plurality of continuous filaments to individually form at least first leg portions of a first leg, using filaments from a first portion of the predetermined plurality of bobbins to braid the first leg about the first detachable mandrel leg positioned substantially along the longitudinal axis in a braiding zone, the braiding zone being a conical zone defined by the filaments extending from the bobbins to the stent on the mandrel;
   (a)(ii) braiding a second discrete plurality of continuous filaments to individually form at least first leg portions of a second leg, using filaments from a second portion of the predetermined plurality of bobbins to braid the second leg about the second detachable mandrel leg positioned in the braiding zone;
   (b) braiding the first plurality of continuous filaments and the second plurality of continuous filaments together to form a first body portion of the body, using filaments from both portions of the predetermined plurality of bobbins to braid the body about a mandrel body positioned in the braiding zone;

wherein:

the first set of bobbin carriers revolves about a longitudinal axis in a clockwise circumferential direction, the second set of bobbin carriers revolves about the longitudinal axis in a counterclockwise circumferential direction, and the braiding process in step (a) comprises braiding each leg in a 1:1 single filament braiding ratio and configuring each of the first set of bobbin carriers and second set of bobbin carriers with bobbins spaced one bobbin per every other carrier such that each carrier having a bobbin thereon is positioned circumferentially between two empty carriers in that set of bobbin carriers.

20. The process of claim 19 wherein the braiding process in step (b) comprises braiding the body in a 2:2 single filament braiding ratio and configuring both the first set of bobbin carriers and the second set of bobbin carriers with a single bobbin on every carrier.

21. The process of claim 19 wherein the braiding process in step (b) comprises braiding the body in a 1:1-paired filament braiding ratio.

22. The process of claim 21 further comprising configuring the first set of bobbin carriers and the second set of bobbin carriers in a 1:1-in-train configuration.

* * * * *